(12) United States Patent
Yokoi et al.

(10) Patent No.: US 7,578,788 B2
(45) Date of Patent: Aug. 25, 2009

(54) CAPSULE-TYPE MEDICAL DEVICE

(75) Inventors: Takeshi Yokoi, Hino (JP); Hironobu Takizawa, Hachioji (JP); Akio Uchiyama, Saitama (JP); Hitoshi Mizuno, Koganei (JP)

(73) Assignee: Olympus Corporation, Tokyo (JP)

( * ) Notice: Subject to any disclaimer, the term of this patent is extended or adjusted under 35 U.S.C. 154(b) by 196 days.

(21) Appl. No.: 10/395,745

(22) Filed: Mar. 24, 2003

(65) Prior Publication Data

US 2003/0181788 A1    Sep. 25, 2003

(30) Foreign Application Priority Data

Mar. 25, 2002    (JP)    ............... 2002-084387

(51) Int. Cl.
  *A61B 1/06*    (2006.01)
  *A61B 1/04*    (2006.01)
  *A61B 1/00*    (2006.01)

(52) U.S. Cl. ............... 600/160; 600/109; 600/117; 600/118

(58) Field of Classification Search ............... 600/109, 600/117, 128, 160, 424; 348/65, 73
See application file for complete search history.

(56) References Cited

U.S. PATENT DOCUMENTS

| | | | | |
|---|---|---|---|---|
| 3,043,309 A | * | 7/1962 | McCarthy | 604/540 |
| 3,485,237 A | * | 12/1969 | Bedford | 600/581 |
| 4,249,536 A | * | 2/1981 | Vega | 604/98.01 |
| 4,278,077 A | * | 7/1981 | Mizumoto | 600/109 |
| 4,832,051 A | * | 5/1989 | Jarvik et al. | 607/116 |
| 5,269,757 A | * | 12/1993 | Fagan et al. | 604/95.01 |
| 5,353,807 A | | 10/1994 | DeMarco | |
| 5,681,260 A | * | 10/1997 | Ueda et al. | 600/114 |
| 5,989,230 A | * | 11/1999 | Frassica | 604/264 |
| 6,240,312 B1 | * | 5/2001 | Alfano et al. | 600/476 |
| 6,324,418 B1 | * | 11/2001 | Crowley et al. | 600/476 |
| 6,547,723 B1 | * | 4/2003 | Ouchi | 600/146 |
| 6,682,473 B1 | * | 1/2004 | Matsuura et al. | 600/29 |
| 6,702,734 B2 | * | 3/2004 | Kim et al. | 600/114 |
| 2001/0051766 A1 | * | 12/2001 | Gazdzinski | 600/309 |
| 2002/0109774 A1 | * | 8/2002 | Meron et al. | 348/74 |
| 2002/0198439 A1 | * | 12/2002 | Mizuno | 600/109 |

(Continued)

FOREIGN PATENT DOCUMENTS

JP    07-11985    *    5/1995

(Continued)

*Primary Examiner*—John P Leubecker
*Assistant Examiner*—Philip R Smith
(74) *Attorney, Agent, or Firm*—Scully, Scott, Murphy & Presser, P.C.

(57) ABSTRACT

A capsule-type medical device comprises a capsule main unit having functions for being inserted into the body cavity and performing medical acts such as taking images or the like. The capsule main unit comprises therein a magnet which is acted upon by external magnetism, and a spiral portion on the outer perimeter, so that rotating force acting upon the magnet is readily converted into a propelling force for propelling the capsule-type medical device. A flexible insertion portion which is long and small in diameter is provided to the capsule main unit to allow smooth progression through the body cavity, and the center of gravity of the device is placed upon the longitudinal center axis of the capsule main unit, thus facilitating smooth progression through the body cavity.

20 Claims, 18 Drawing Sheets

U.S. PATENT DOCUMENTS

2003/0120130 A1* 6/2003 Glukhovsky et al. ........ 600/109
2003/0167000 A1* 9/2003 Mullick et al. .............. 600/424
2003/0216639 A1* 11/2003 Gilboa et al. ............... 600/424
2004/0260150 A1* 12/2004 Bernstein ................... 600/139

FOREIGN PATENT DOCUMENTS

| JP | 3017770 | 12/1999 |
|----|---------|---------|
| JP | 2001-179700 | 7/2001 |

* cited by examiner

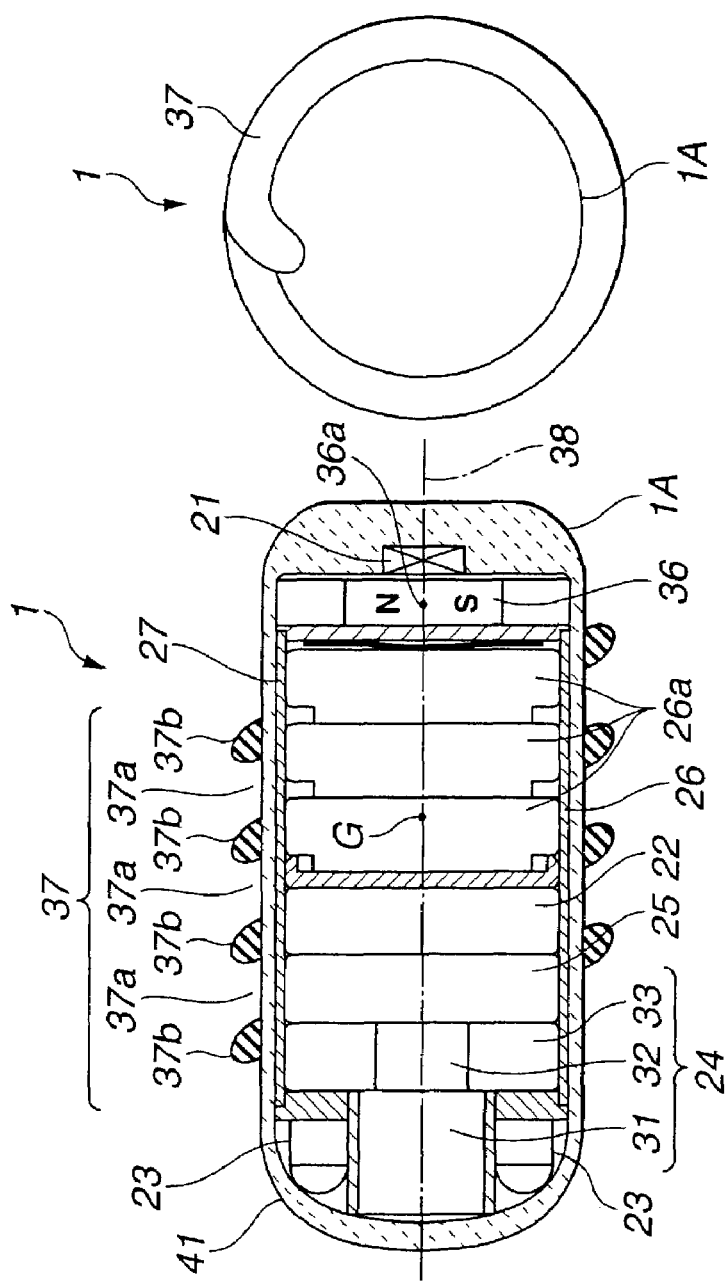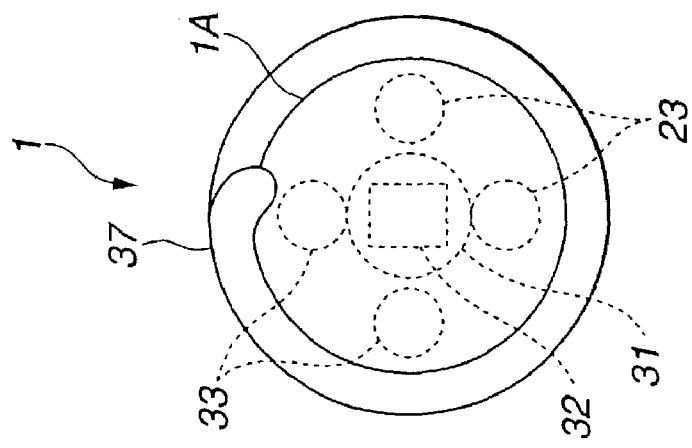

ULTRASONIC TOMOGRAPHIC PLANE (360°)

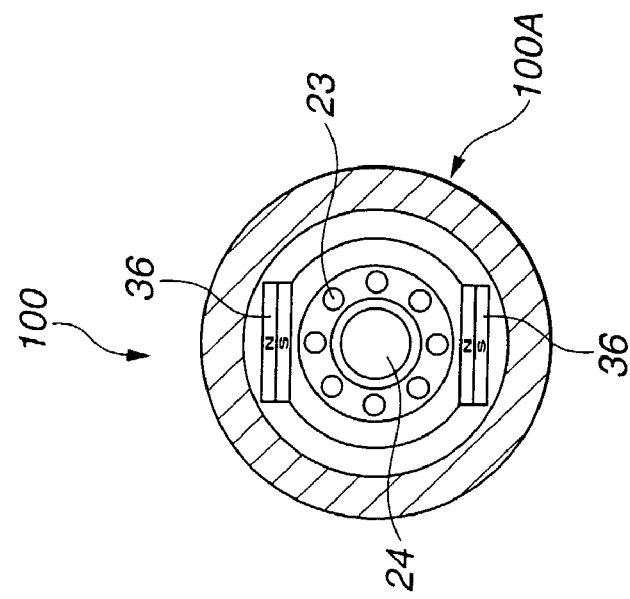
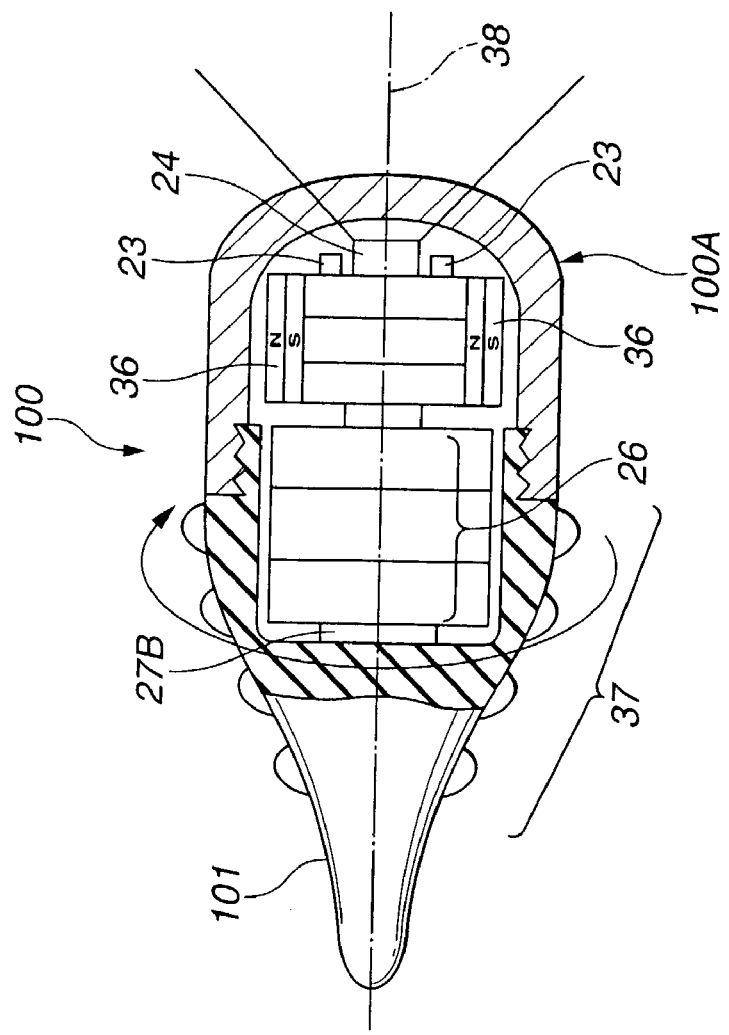

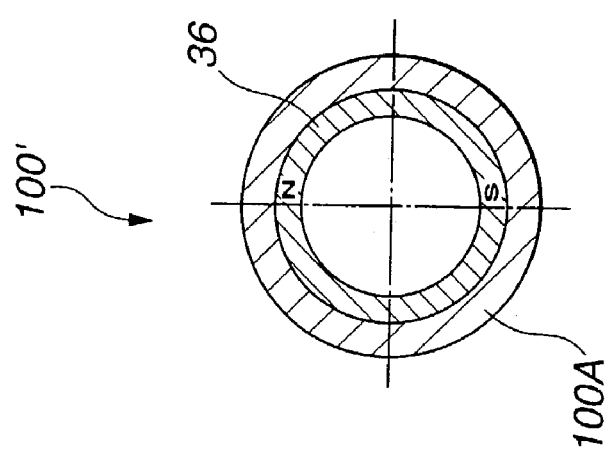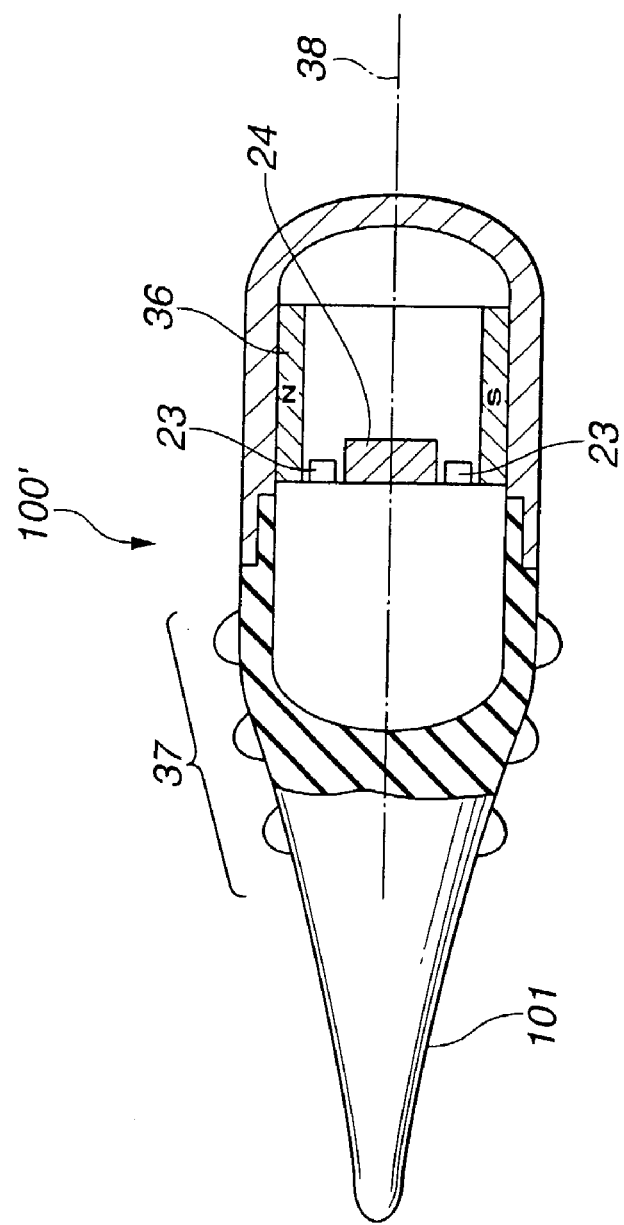

CAPSULE-TYPE MEDICAL DEVICE

This application claims benefit of Japanese Application No. 2002-84387 filed on Mar. 25, 2002, the contents of which are incorporated by this reference.

BACKGROUND OF THE INVENTION

1. Field of the Invention

The present invention relates to a capsule-type medical device which is passed through the body cavity and is capable of examination, therapy, and/or treatment.

2. Description of the Related Art

Capsule-type medical devices are known as medical devices which are swallowed by patients to pass through the body cavity tract, which can perform examination, therapy, and/or treatment.

Such capsule-type medical devices comprise treatment tools for performing such medical treatment, such as a medication-depositing unit for depositing medicine, treatment devices such as forceps or the like, treatment devices for performing incision or coagulation by ultrasonic or high-frequency means, and so forth, and are arranged to perform such medical treatment at an object portion in the body cavity tract. However, there are shortcomings within the capsule-type medical devices, such as requiring a long time to reach the object portion unless guided through the body cavity tract.

To deal with this problem, Japanese Patent Publication No. 3017770 discloses a capsule-type medical device comprising a magnet which is magnetically manipulated by a magnet outside of the body of the subject. With the medical device described in Japanese Patent Publication No. 3017770 (hereafter referred to simply as "No. 3017770"), an external uniform magnetic field uniaxially acts upon magnets provided on the outer perimeter of a capsule main body in the vertical direction, so that the capsule is guided through the body cavity tract without rotating, primarily. Also, an arrangement is also disclosed wherein an alternating magnetic field is applied externally, so as to rotate the main body. However, efficiently propelling rotational motion of the main unit is not easy.

Note that this No. 3017770 is equivalent to the Japanese Patent Application with Application No. H2-109696 (filed on Apr. 25, 1990) which is cited as proof of prior application in the later-described U.S. Pat. No. 5,681,260.

On the other hand, with the capsule-type medical device described in Japanese Unexamined Patent Application Publication No. 2001-179700 (hereafter referred to simply as "No. 2001-179700"), an external rotating magnetic field acts triaxially on a magnet provided within the capsule main unit in the vertical direction and horizontal direction, so as to gain propulsion by rotationally turning.

With the capsule-type medical device described in No. 2001-179700, a thrust generating unit which obtains propulsion by rotating is provided in the capsule main unit. However, with the capsule-type medical device described in No. 2001-179700, no consideration has been given to the internal structure of the capsule main unit with regard to rotations of the capsule main unit.

Accordingly, the capsule-type medical device described in No. 2001-179700 may make useless motions such as rotating eccentrically (zigzagging), and accordingly take time to reach the object position in the body cavity tract, rather than reaching the location smoothly.

Also, U.S. Pat. No. 5,353,807 discloses a configuration comprising a slender and flexible recovery member, a main unit disposed on the tip thereof for performing medical treatment, a coil provided on the circumference to the main unit for guiding with an eternal magnetic flux, and multiple propulsion plates provided on the recovering member, thereby enabling the direction of the main unit to be controlled by the magnetic polarity generated by the coil and the external magnetic flux, and further guiding the main unit through the body cavity by a propulsion plate provided on the recovering member.

This patent also discloses an arrangement of a main unit comprising an internal magnet and battery, with the capsule not being provided with the recovering member but rather guided by the external magnetic field.

However, with the arrangement described in this U.S. Patent, the direction of the magnetic polarity generated by the coil or the magnet is in the longitudinal direction of the main unit, so smooth propulsion by an external magnetic field is not easy.

Also, U.S. Pat. No. 5,681,260 also discloses a device wherein an endoscope insertion portion or the like is magnetically guided through the body cavity, besides the embodiment relating to FIGS. 50 through 76B corresponding to No. 3017770.

The arrangement described in this U.S. patent has a similar configuration as that in No. 3017770, and smooth propulsion of the endoscope insertion portion or the like is not easy.

Further, the above-described preceding examples do not disclose contents corresponding to the Claims of the Present Invention.

SUMMARY OF THE INVENTION

Accordingly, it is an object of the present invention to provide a capsule-type medical device with little useless motions such as eccentric rotations, and which can be smoothly and readily propelled through body cavities.

It is another object of the present invention to provide a capsule-type medical device which can be readily propelled through bending body cavities.

To achieve these objects, the capsule-type medical device according to the present embodiment comprises: a capsule main unit provided with functions for performing medical acts such as examination, therapy, and/or treatment; a magnet provided to the capsule main unit, for magnetically acting upon an external magnet outside of the subject; and a propulsion generating unit for converting rotational motion due to the magnet into propelling force; wherein the center of gravity of the capsule main unit generally matches the center axis of the capsule main unit in the longitudinal direction, thereby suppressing useless motions such as eccentric rotations, and enabling the capsule-type medical device to be smoothly propelled through the body cavity to the target position.

BRIEF DESCRIPTION OF THE DRAWINGS

FIGS. 1 through 14B relate to a first embodiment of a present embodiment, wherein FIG. 1 is an overall configuration diagram illustrating a medical system with the first embodiment of the present invention;

FIG. 2 is a block diagram illustrating the configuration of the electrical system according of the capsule-type medical device according to the first embodiment;

FIG. 3A is a cross-sectional diagram illustrating the configuration of the capsule-type medical device;

FIG. 3B is a frontal view illustrating the tip side of the arrangement shown in FIG. 3A;

FIG. 3C is a rear side view illustrating the rear end view of the arrangement shown in FIG. 3A;

FIGS. 10A through 10C show a configuration wherein the capsule main unit can be divided into the two parts of a portion where an observation device is disposed, and a portion where a magnet and spiral portion are disposed, wherein FIG. 10A is an explanatory diagram illustrating a capsule-type medical device wherein the observation field of view of the observation device is directed backwards;

FIG. 10B is an explanatory diagram illustrating a capsule-type medical device wherein the observation field of view of the observation device is directed diagonally backwards;

FIG. 10C is an explanatory diagram illustrating a capsule-type medical device wherein the observation field of view of the observation device is directed toward the side;

FIG. 11A is an explanatory diagram illustrating a capsule-type medical device wherein a portion to which a spiral portion is provided is formed at a flexible insertion portion;

FIG. 11B is a transverse cross-sectional diagram of the arrangement shown in FIG. 11A;

FIG. 12A is an explanatory diagram illustrating a capsule-type medical device provided with a ring-shaped magnet;

FIG. 12B is a transverse cross-sectional diagram of the arrangement shown in FIG. 12A;

FIGS. 13A through 13C illustrate a capsule-type medical device wherein a spiral portion is provided on the opposite side as to a flexible insertion portion on one end of the capsule main unit which is the progression direction thereof in the longitudinal direction, wherein FIG. 13A is an explanatory diagram illustrating a capsule-type medical device wherein the spiral portion is provided over almost the entire circumference of the rear side of the capsule main unit;

FIG. 13B is an explanatory diagram illustrating a capsule-type medical device wherein the spiral portion is provided diagonally over half of the rear side of the capsule main unit so as to enable diagonally viewing in the backward direction;

FIG. 13C is an explanatory diagram illustrating a capsule-type medical device wherein the spiral portion is provided over half of the rear side of the capsule main unit so as to enable viewing sideways;

FIG. 14B is an explanatory diagram illustrating that the flexible insertion portion is bendable in the direction generally orthogonal to the longitudinal direction;

FIGS. 15 through 21 relate to a second embodiment of the present invention, wherein FIG. 15 is an explanatory diagram illustrating a capsule-type medical device according to the second embodiment of the present invention;

FIG. 16 is an explanatory diagram illustrating the operations of the capsule-type medical device shown in FIG. 15 within the body cavity;

FIG. 17 is an explanatory diagram illustrating the relation between the length of the rigid portion of the capsule main unit and the length of the soft portion of the flexible insertion portion, with regard to the maximum diameter of the tubular body cavity organ;

FIG. 18 is an explanatory diagram of the operations of the capsule-type medical device shown in FIG. 15 in bent or narrow portions or the like in tubular body cavity organs;

FIG. 19 is an external diagram illustrating a capsule-type medical device wherein the spiral portion is formed by adhesion and fixing of a wire-like material to the outer perimeter of the flexible insertion portion;

FIG. 20 is an explanatory diagram illustrating a capsule-type medical device wherein the flexible insertion portion is configured with multiple ball-shaped protrusions formed with ball-shaped magnets built therein, formed thereupon;

FIG. 21 is an explanatory diagram illustrating the operations of the capsule-type medical device shown in FIG. 20 inside the body cavity;

FIGS. 22 and 23 relate to a third embodiment of the present invention, wherein FIG. 22 is an explanatory diagram illustrating a capsule-type medical device according to the third embodiment of the present invention; and FIG. 23 is an explanatory diagram illustrating a modification example of the capsule-type medical device shown in FIG. 22.

DESCRIPTION OF THE PREFERRED EMBODIMENTS

The following is a description of embodiments of the present invention, with reference to the drawings.

First Embodiment

A first embodiment of the present invention will be described with reference to FIGS. 1 through 14B. The primary object of the present embodiment is to provide a device and method wherein a capsule-type medical device which performs medical actions can be rotated by external magnetism and thus be smoothly guided to a target portion or beside a target portion; more specifically, to provide a device and method wherein eccentric motion in rotation is suppressed so as to enable effective or smooth propulsion to beside the target portion.

Figure 1:
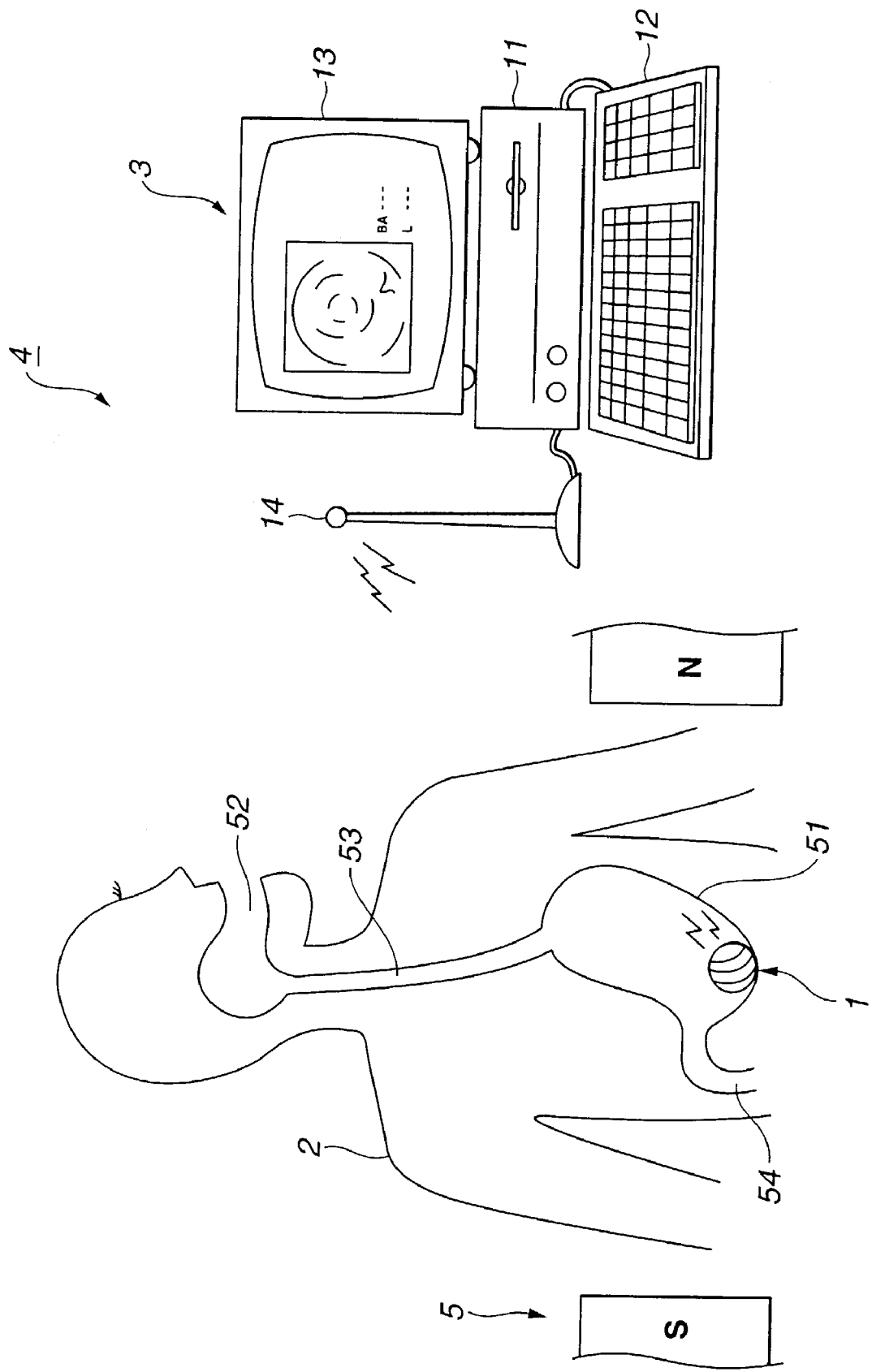

As shown in FIG. 1, a capsule-type medical device 1 exchanges radio waves with a capsule control device (hereafter referred to simply as "control device") 3 while passing through the body cavity tract of a patient 2, thus configuring a medical system 4 enabling examination, therapy, and/or treatment, under control of this control device 3.

The medical system 4 is for performing screening of the esophagus, duodenum, small intestine, large intestine, etc., by swallowing the capsule-type medical device 1 with water or the like in the same way that one would swallow medicine, following precleaning of the large intestine (lavage of the intestinal tract). In the event that the capsule-type medical device 1 passes through an area of interest rapidly, as with the duodenum for example, the medical system 4 takes images at a rate of 10 frames per second, and on the other hand, takes images at 2 frames per second for areas passed through slowly, such as the small intestine, for example. The images that are taken are subjected to necessary signal processing and digital compression processing and then transmitted to the control device 3, and only information necessary is recorded as moving images so as to be used for diagnosis.

Also, the medical system 4 is configured comprising a magnetic guiding device 5 which magnetically guides the capsule-type medical device 1. Note that FIG. 1 only shows the magnetic guiding device 5 schematically. The magnetic guiding device 5 is configured so as to form a rotating magnetic field which magnetically acts upon a later-described magnet provided in a capsule main unit 1A of the capsule-type medical device 1. Also, the magnetic guiding device 5 is connected to the control device 3, such that the control device 3 can control the direction of the generated rotating magnetic field.

The control device 3 comprises a personal computer main unit 11 having functions for controlling the capsule-type medical device 1 and the magnetic guiding device 5, a keyboard 12 which is connected to the personal computer main unit 11 for inputting commands, data, etc., a monitor 13 which is connected to the personal computer main unit 11 for displaying images and the like, and an external antenna 14 which is connected to the personal computer main unit 11 for transmitting control signals for controlling the capsule-type medical device 1 and receiving signals from the capsule-type medical device 1.

The control device 3 is arranged such that the control signals for controlling the capsule-type medical device 1 and the magnetic guiding device 5 are generated based on key input from the keyboard 12 or by a control program stored in a hard disk or the like within the personal computer main unit 11.

The control signals for controlling the magnetic guiding device 5 are transmitted from the external computer main unit 11 to the magnetic guiding device 5 by a connecting cable not shown in the drawings.

The magnetic guiding device 5 generates the rotating magnetic field wherein the direction of the rotating magnetic field is controlled, based on the transmitted control signals. The capsule-type medical device 1 is configured such that the rotating magnetic field generated by the magnetic guiding device 5 magnetically acting upon the later-described magnet rotates the capsule main unit 1A such that the direction of progression of the capsule main unit 1A within the body cavity is set by a later-described propulsion generating unit, and also such that motive energy for propulsion of the capsule main unit 1A is generated.

On the other hand, the control signals for controlling the capsule-type medical device 1 are modulated by carrier waves of a predetermined frequency at an oscillating circuit within the personal computer main unit 11, and transmitted as radio waves from the external antenna 14.

The capsule-type medical device 1 receives the radio waves with a later-described wireless antenna 21, the control signals are demodulated, and the demodulated control signals are output to the component circuits and the like.

Also, the control device 3 receives signals including image information of video signals and the like transmitted from the wireless antenna 21 of the capsule-type medical device 1 with the external antenna 14, and displays images and the like on the monitor 13.

Figure 2:
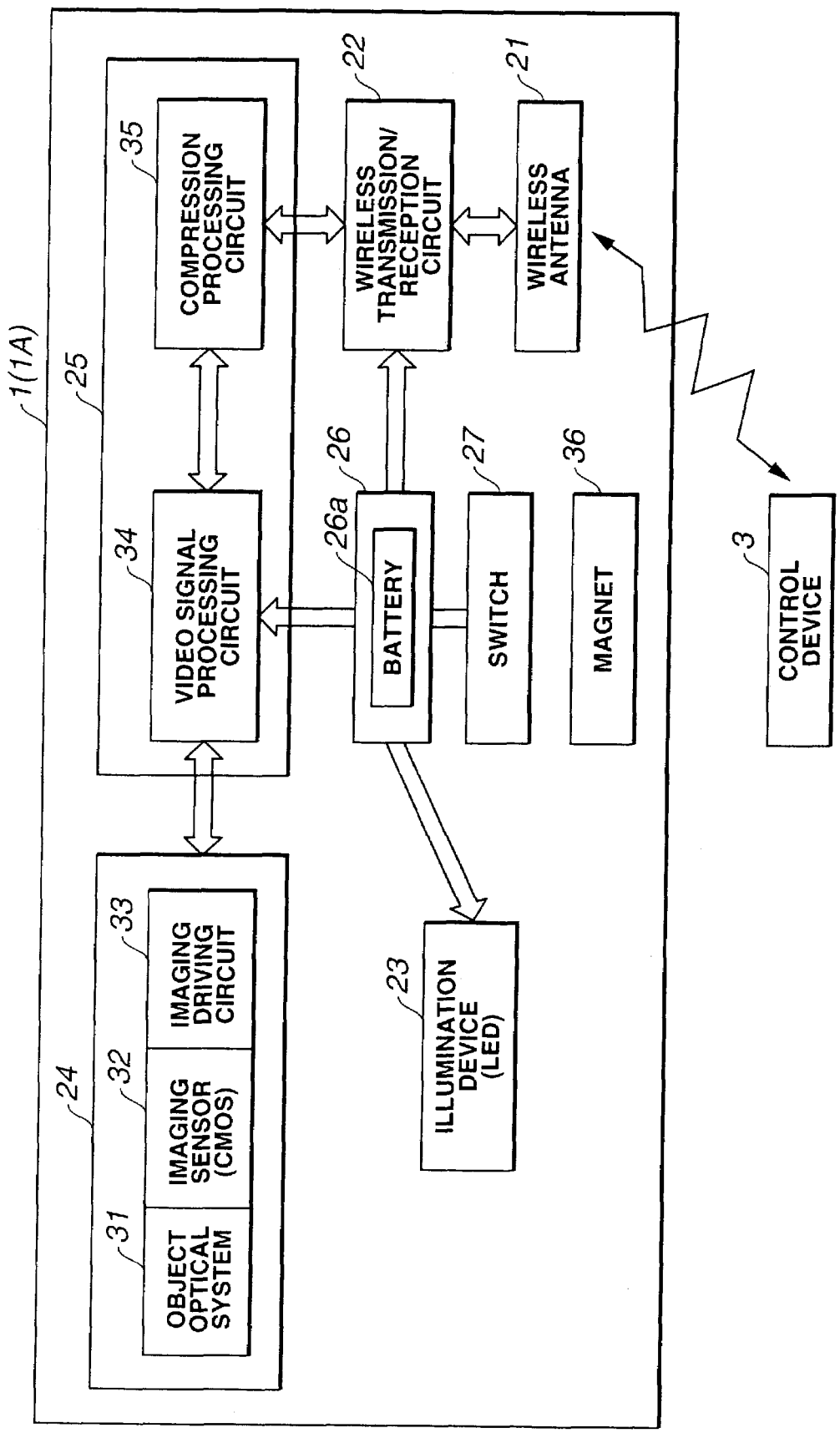

Next, a detailed configuration of the capsule-type medical device according to the present embodiment will be described with reference to FIGS. 2 through 3C. Note that the present embodiment is a capsule-type medical device capable only of examination (observation).

The capsule-type medical device 1 is primarily configured of a wireless antenna 21 which exchanges radio waves with the control device 3, a wireless transmission/reception circuit 22 which subjects the radio waves exchanged with the wireless antenna 21 to signal processing, an illumination device 23 of LEDs (Light-Emitting Diodes) or the like which emits illumination light for illuminating the body cavity, an observation device (imaging device) 24 for acquiring optical images of the body cavity illuminated with the illumination light from the illumination device 23 so as to take images, a digital signal processing circuit 25 for performing digital signal processing or the like with regard to the imaging signals obtained from the imaging device 24, a battery unit 26 where a battery 26a of some sort is stored, and a switch 27 which turns electrical power supplied from the battery unit 26 off and on.

The wireless transmission/reception circuit 22 selectively extracts carrier waves of the radio waves received from the control device 3 using the wireless antenna 21, and performs detection, demodulation of control signals, and output thereof to the component circuits, as well as modulating information signals such as video signals or the like from the component circuits with carrier waves of a predetermined frequency, and transmitting these from the wireless antenna 21 as radio waves.

The observation device 24 is configured of an object optical system 31 for acquiring optical images, an imaging sensor 32 such as a CMOS (Complementary Metal-Oxide Semiconductor) or the like for imaging the optical images acquired by the object optical system 31, and an imaging driving circuit 33 for driving the imaging sensor 32.

The digital signal processing circuit 25 is configured of a digital video signal processing circuit (hereafter referred to as "video signal processing circuit") 34 which subjects the imaging signals taken by the imaging sensor 32 to signal processing and converts these into digital video signals, and a digital compression processing circuit (hereafter referred to as "compression processing circuit") 35 which subjects the converted digital video signals to compression processing.

The battery unit 26 supplies electric power from the stored battery 26a to the illumination device 23, the digital signal processing circuit 25, and the wireless transmission/reception circuit 22 through the switch 27. Note that the observation device 24 is supplied electric power from the battery 26a via the digital signal processing circuit 25.

Also, the capsule-type medical device 1 has built in a permanent magnet (hereafter referred to simply as "magnet") 36 upon which the rotating magnetic field, generated by the magnetic guiding device 5 as described above, acts. The magnet used there is a permanent magnet such as a neodymium magnet, samarium-cobalt magnet, ferrite magnet, iron-chromium-cobalt magnet, platinum magnet, Alnico (AlNiCo) magnet, and so forth.

Rare-earth magnets such as neodymium magnets and samarium-cobalt magnets have strong magnetism and are advantageous in reducing the size of the magnet built into the capsule main unit 1A. On the other hand, ferrite magnet are advantageous in that the cost is low. Further, platinum magnets have excellent corrosion resistance, and are suitable for medical purposes.

Also, the magnet 36 built into the capsule main unit 1A needs not be a permanent magnet, and rather may be formed of a coil instead. In this case, the capsule main unit 1A may generate magnetism at the coil by current from an electric power source such as a built-in battery or the like, or the coil may be magnetized by electric power temporarily stored in an built-in capacitor or the like.

Further, instead of a built-in power source, the capsule main unit 1A may have a coil built in which is used to generate electricity, which is stored in a capacitor and used to magnetize a separate coil. In this case, the limit on capacity of a built-in battery is done away with for the capsule main unit 1A, thereby enabling operations over long periods of time. Also, the same coil may be used for the coil for generating electricity and the magnetizing coil.

As shown in FIGS. 3A through 3C, the capsule-type medical device 1 has a cylindrical capsule main unit 1A covered with a transparent main unit exterior member 41 in an airtight manner, with components built in such as the above-described illumination device 23 and observation device 24 being positioned within the cylindrical capsule main unit 1A. More specifically, the object optical system 31 making up the observation device 24 is positioned at the center portion of the tip side of the cylindrical capsule main unit 1A of the capsule-type medical device 1, and the imaging sensor 32 is positioned at the image focus location of the object optical system 31.

The imaging driving circuit 33 is formed so as to surround the imaging sensor 32. The digital signal processing circuit 25 is positioned at the base side of the imaging driving circuit 33 and the imaging sensor 32, with the wireless transmission/reception circuit 22 disposed at the base side of the digital signal processing circuit 25.

Also, the illumination device 23 is formed so as to surround the object optical system 31, thereby illuminating in front of the capsule main unit 1A with illumination light through the transparent main unit exterior member 41. As shown in FIG. 3B, the illumination device 23 is configured of an array of four white LEDs, for example.

The battery unit 26 is provided on the rear side of the wireless transmission/reception circuit 22, with three batteries 36a such as button batteries stored in the battery unit 26. Upon the battery unit 26 being turned on by the switch 27 being operated externally, an operation which is not indicated in the drawings, electric power is supplied to the illumination device 23 and the like through the switch 27. The magnet 36 is positioned behind the battery unit 26, with the wireless antenna 21 positioned further behind.

The capsule-type medical device 1 has the above-described built-in components reinforced and held by a cylindrical member such as a metal ring reinforcing member not shown in the drawings, and placed in the main unit exterior member 41. The capsule-type medical device 1 is formed to a size wherein the patient 2 can swallow the capsule main unit 1A without much trouble.

Also, the capsule-type medical device 1 has the magnet 36 disposed therein such that the poles N and S are perpendicular to the center axis 38 in the longitudinal direction of the cylindrical shape of the capsule main unit 1A, as shown in FIG. 3A (i.e., in FIG. 3A, the center axis 38 is horizontal, and the direction of magnetic polarity is vertical, which is perpendicular thereto).

Thus, with the capsule-type medical device 1, upon the rotating magnetic field generated by the magnetic guiding device 5 acting upon the magnet 36, the capsule main unit 1A rotates on the longitudinal center axis 38 due to the magnet 36 being acted upon.

Also, the capsule-type medical device 1 is provided with a propulsion generating unit on the outer perimeter of the capsule main unit 1A, which is a spiral portion 37 made up of spiral grooves 37a through which fluids such as gas and liquids in the body cavity can flow through in either direction, and spiral ridges 37b where portions next to the spiral grooves 37a protrude in a spiraling manner. Note that the spiral ridges 37b are formed with curved faces so as to smoothly come into contact with the inner walls of the body cavity.

Providing such a spiral portion 37 allows the capsule-type medical device 1 to move forward or backwards according to rotations of the capsule main unit 1A, since rotations are converted into propulsion force as the fluids such as gas and liquids in the body cavity pass through the spiral grooves 37a making up the spiral portion 37.

Also, the capsule main unit 1A can be propelled following the spirals upon rotation, by using the friction between the protrusions of the spiral ridges 37b making up the spiral portion 37 and the mucous membranes.

That is to say, in the event that the protrusions of the spiral ridges 37b come into contact with the inner walls, and the capsule main unit 1A is rotated in that state, the capsule main unit 1A rotates in a state wherein spinning free is restricted by the friction at the point of contact, so the rotations propel the capsule main unit 1A in spiral fashion as to the inner walls. Reversing the direction of rotation allows the direction or progression of the capsule main unit 1A to be reversed.

Let us say that the spiral protrusions formed for the spiral ridges 37b are cyclically formed with a pitch of p, for example. In a normal state of use wherein the spiral ridges 37b are in contact with the tubular inner walls, one rotation of the capsule main unit 1A propels the capsule main unit 1A by the pitch p.

Note that the capsule-type medical device 1 is capable of changing the direction in which it is traveling according to the direction of rotation in which the capsule main unit 1A rotates so as to match the rotating plane of the magnet 36 and the rotating plane of the rotating magnetic field according to the rotation of the rotating magnetic field.

Generally, with such a capsule-type medical device 1, the capsule main unit 1A may make useless motions such as eccentric motion (zigzagging) unless the center of gravity is not generally upon the longitudinal center axis 38 of the capsule main unit 1A.

With the present embodiment, the capsule-type medical device 1 is configured such that the batteries 27a such as button batteries or the like, which are the heaviest built-in components, are positioned on the center axis 38 close to the center in the longitudinal direction, and the center 36a of the direction of magnetism of the magnet 36 is positioned on the center axis 38 of the capsule main unit 1A, so that the center of gravity G of the capsule main unit 1A is generally on the center axis 38 of the capsule main unit 1A, as shown in FIG. 3A.

Figure 3D:
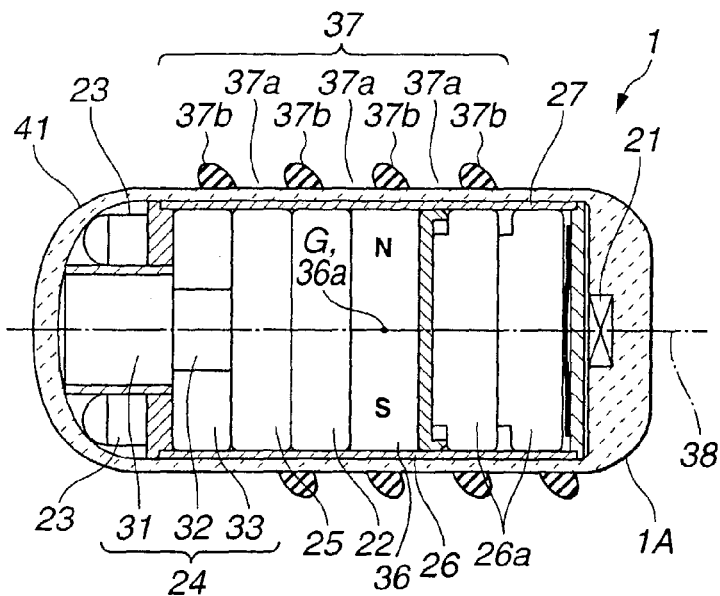
FIG. 3D is a cross-sectional view illustrating the configuration of the capsule-type medical device with the placement position of the magnet changed.

Also, the built-in components may be arranged so as to match the center of gravity G of the capsule main unit 1A by changing the position of the magnet 36 shown in FIG. 3A such that the center 36a of the direction of magnetism of the magnet 36 is positioned on the center axis 38 of the capsule main unit 1A, as with the capsule-type medical device 1 shown in FIG. 3D.

Configuring the capsule-type medical device 1 thus enables smooth guiding to the target position through the tubular body cavity or lumen without useless motions such as eccentric movement (zigzagging) of the capsule main unit 1A.

Next, the operations of the capsule-type medical device 1 according to the present invention will be described.

As shown in FIG. 1, in the event that there is the need to observe a body cavity tract such as the stomach 51 for example, of the patient 2, for long periods of time, the operator has the patient swallow the capsule-type medical device 1, and causes the device to pass through the stomach. Immediately prior to having the patient 2 swallow the capsule-type medical device 1, the operator turns the switch 27 thereof on, so that electric power from the batteries 26a in the battery unit 26 is supplied to the illumination device 23, the observation device 24, the digital signal processing circuit 25, and the wireless transmission/reception circuit 22.

At the same time, the operator activates (turns on) the magnetic guiding device 5, and magnetically controls the capsule-type medical device 1 with the rotating magnetic field generated by the magnetic guiding device 5 so that the capsule-type medical device 1 reaches the target portion.

As described above, with the capsule-type medical device 1, upon the rotating magnetic field generated by the magnetic guiding device 5 acting upon the magnet 36, the capsule main unit 1A is rotated by the force which the magnet 36 receives.

Then, the rotational force of the capsule main unit 1A is converted into propulsion and the capsule-type medical device 1 proceeds forwards or retreats backwards, due to at least one of: fluids such as gas and liquids in the body cavity passing through the spiral grooves 37a; and the spiral ridges 37b smoothly coming into contact with the inner walls of the body cavity. Further, in the event that the capsule main unit 1A comes into contact with the inner walls of the body cavity, the capsule main unit 1A is held by friction between the mucous membranes on the inner walls of the body cavity and the spiral ridges 37b, so rotations in this state are converted into greater propulsion force for proceeding forwards or retreating backwards. The capsule-type medical device 1 is capable of changing the direction in which it is traveling by the capsule main unit 1A rotating with the rotating plane of the magnet 36 matching the rotating plane of the rotating magnetic field, according to the rotation of the rotating magnetic field.

Moreover, the capsule-type medical device 1 is capable of smoothly moving through the lumen to the target position without the capsule main unit 1A making useless motions such as eccentric movement.

The capsule-type medical device 1 passes through the oral cavity 52 and the esophagus 53, and reaches the stomach 51. Now, the major axial diameter of the esophagus 53 is 16 mm and the minor axial diameter thereof is 14 mm, for example, so the capsule-type medical device 1 can easily pass through if formed with a generally circular cross-section 14 mm or less in outer diameter.

In the event that there is the need to observe the inside of the stomach 51, the operator performs input corresponding to a command for staring observation, from a keyboard 12 for example of the control device 3. Control signals from this key input are emitted as radio waves from the external antenna 14 of the control device 3, and transmitted to the capsule-type medical device 1.

The capsule-type medical device 1 detects operation-start signals from the signals received with the wireless antenna 21, and drives the wireless transmission/reception circuit 22, illumination device 23, observation device 24, and digital signal processing circuit 25.

The illumination device 23 emits illumination light in the direction of the field of view of the observation device 24, the optical image of the range of the field of view illuminated is imaged on the imaging sensor 32 of the observation device 24, subjected to photo-electric conversion, and an imaging signal is output. This imaging signal is converted into digital video signals at the video signal processing circuit 34 of the digital signal processing circuit 25, subjected to compression processing at the digital compression processing circuit 35 and modulated at the wireless transmission/reception circuit 22, and emitted from the wireless antenna 21 as radio waves.

The radio waves are received with the external antenna 14 of the control device 3, demodulated with the reception circuit within the personal computer main unit 11, converted into digital signals with an A/D converter within the personal computer main unit 11, and stored in memory, while also read out at a predetermined speed with an optical image taken with the imaging sensor 32 being displayed in color on the monitor 13. The operator can observe the inside of the stomach 51 of the patient 2 by observing this image. The operator can further readily control how the external magnetic field is applied so that the entire stomach region can be observed, using operating means such as a joystick provided outside the body while observing the observation image. The optical image can also be recorded in an unshown image recording device.

Following observation of the stomach 51, the capsule-type medical device 1 is magnetically guided by the rotating magnetic field formed by the magnetic guiding device 5 as described above, so as to pass from the stomach 51 through the duodenum 54, the small intestine and large intestine which are not shown, and to be extracted from the anus. During this time, the capsule-type medical device 1 can observe the interior of the entire digestive tract.

Due to the configuration of the present embodiment, the capsule-type medical device 1 can suppress useless motions of the capsule main unit 1A such as eccentric movement (zigzagging), enabling effective and smooth propulsion through the lumen to beside the target portion.

Also, no useless motions means that the magnetic guidance of the capsule-type medical device 1 is more effective, thus yielding the great advantage that one or both of the magnet 36 within the capsule and the external magnet or electromagnet can be reduced in size.

Also, the medical acts can be completed in a short time by propelling the capsule-type medical device 1 smoothly and efficiently.

Figure 4A:
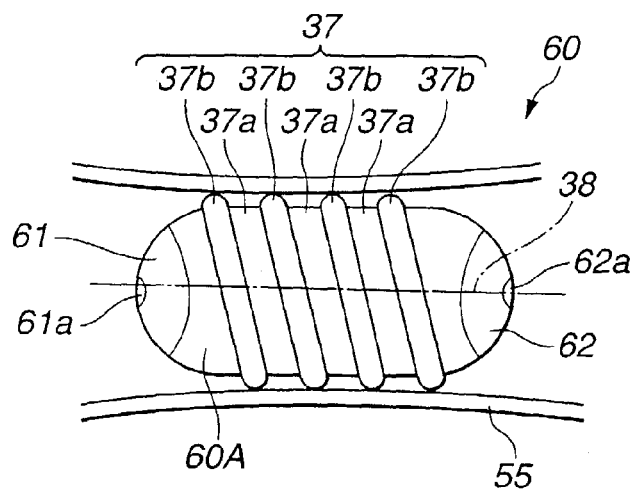
FIG. 4A is an external explanatory diagram of a capsule-type medical device for spreading a medicine.
Figure 4B:
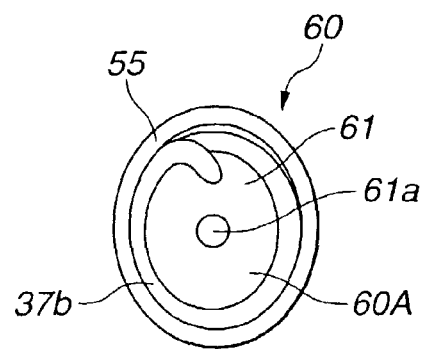
FIG. 4B is an external view of the tip side of the capsule-type medical device shown in FIG. 4A.

Also, the capsule-type medical device may be configured for spreading medicine, as shown in FIGS. 4A and 4B. That is to say, the capsule-type medical device 60 is configured having a medicine spreading opening 61a provided at the tip side so as to enable spreading of medicine stored in a medicine storing unit 61 within the capsule main unit 60A.

Further, the capsule-type medical device 60 is configured to take body fluid samples. That is, the capsule-type medical device 60 is configured having a body fluid injecting opening 62a on the rear end so as to take samples of body fluid into a body fluid storing unit 62 within the capsule main unit 60A. Opening and closing of the openings 61a and 62a is performed by communication control from the control device 3.

Thus, the capsule-type medical device 60 is capable of discharging and spreading medicine stored in the medicine storing unit 61 from the medicine spreading opening 61*a* to a target portions, and also is capable of taking samples of body fluid from the fluid injecting opening 62*a* into the body fluid storing unit 62.

Also, it is needless to say that the medicine storing unit 61 may store a hemostatic agent for stopping bleeding, a ferrofluid or fluorescent agent which is safe to use with human bodies to externally determine hemorrhaging portions, and so forth, besides storing medicine.

Also, the capsule-type medical device 60 may be arranged to mix medicine stored in the medicine storing unit 61 with the body fluid taken in from the fluid injecting opening 62*a*, and ejecting and spreading this mixture from the medicine spreading opening 61*a*.

Note that this capsule-type medical device 60 has a spiral portion 37 formed on the outer perimeter of the capsule main unit, in the same way as with the capsule-type medical device 1 shown in FIG. 3A. Also, the capsule-type medical device 60 has the center of gravity thereof generally upon the longitudinal center axis 38.

Figure 5A:
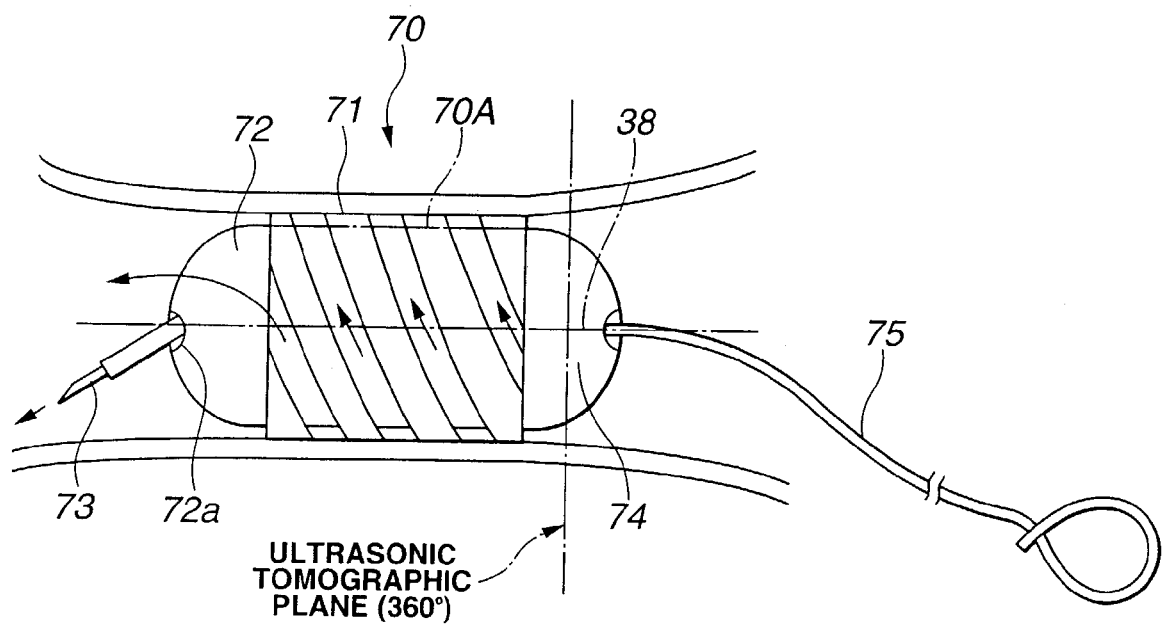
FIG. 5A is an explanatory diagram illustrating a capsule-type medical device comprising a treatment tool storage unit and ultrasonic unit, wherein an elastic rubber cover having a spiral groove formed thereupon is detachably mounted to the capsule main unit.
Figure 5B:
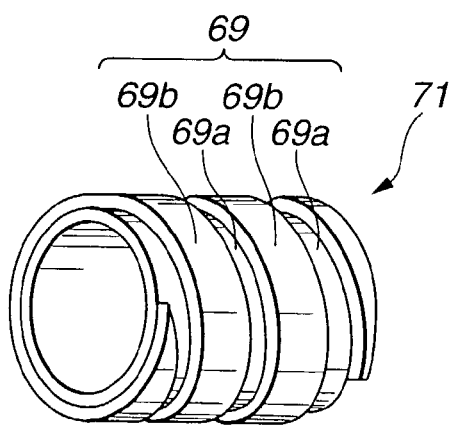
FIG. 5B is a perspective view illustrating a part of the elastic rubber cover shown in FIG. 5A.

Also, the capsule-type medical device 60 may be configured such that an elastic rubber cover having a spiral groove formed thereupon is detachably mounted to the capsule main unit as an exterior member, as shown in FIGS. 5A and 5B. That is to say, as shown in FIG. 5A, the capsule-type medical device 70 is configured such that an elastic rubber cover 71 having spiral grooves 69*a* (see FIG. 5B) formed thereupon can be detachably mounted to the capsule main unit 70A. Thus, the capsule-type medical device 70 enables fluids such as gas and liquids in the body cavity to pass through the spiral grooves 69*a* of the elastic rubber cover 71 to the tip and rear sides thereof.

Also, the thick potions of the elastic rubber cover 71 having a shape like a belt wound thereupon forms the spiral ridges 69*b*, thus forming the spiral portion 69.

The capsule-type medical device 70 has a treatment tool storing portion 72 capable of therapy or treatment within the capsule main unit 70A, and has a treatment tool opening 72*a* formed on the tip thereof. This treatment tool opening 72*a* is plugged with a soluble film such as gelatin which is digested by stomach fluid or a fatty acid which is digested by intestinal fluid, for example. The capsule-type medical device 70 is arranged to open the treatment tool opening 72*a* when reaching near the target portion.

The treatment tool 73 stored in the treatment tool storing portion 72 is capable of extending the tip thereof from the treatment tool opening 72*a* and retracting therein, and can perform therapy or treatment on the target portion of the body cavity tract. The treatment tool 73 is operated and controlled by communication control from the control device 3. Specific operations of the treatment tool 73 may be carried out by operating means such as an unshown joystick or mouse or the like connected to the personal computer main unit 11.

Note that in FIG. 5A, the treatment tool 73 shown is an injection needle capable of injecting a hemostatic agent. With the capsule-type medical device 70 in this case, upon confirmation of a hemorrhaging portion with an unshown blood sensor or the observation device 24, operations of the treatment tool 73 such as the hemostatic agent injection needle stored in the capsule main unit 70A are instructed by communication control from the control device 3, and a hemostatic agent such as ethanol or a powder medicine is spread onto the hemorrhaging portion, thereby stopping the bleeding.

Furthermore, the capsule-type medical device 70 comprises an ultrasonic unit 74 capable of examinations in the capsule main unit. The ultrasonic unit 74 is configured of an unshown ultrasonic probe for transmitting and receiving ultrasonic waves and an ultrasonic control circuit for controlling and driving the ultrasonic probe.

The capsule-type medical device 70 has the ultrasonic probe disposed in a watertight manner such that an unshown acoustic lens unit is positioned on the outer face of the rear end of the capsule main unit 70A, such that a 360° ultrasonic tomographic image, for example, is obtained at the rear end side.

Then, with the capsule-type medical device 70, the ultrasonic tomographic image data obtained is modulated at the wireless transmission/reception circuit 22 in the same manner as with the above-described observation image, and is emitted as radio waves from the wireless antenna 21. Thus, the capsule-type medical device 70 is capable of diagnosing whether or not there are abnormalities in the depth-wise direction of deep portions in the body cavity wall, such as in the small intestine 55 or the like. In the event that the capsule-type medical device 70 is configured to have the observation device 24 as well, both the surface and deep portions of the body cavity can be diagnosed at once.

Also, the capsule-type medical device 70 is configured with the capsule main unit 70A having connected thereto a string 75 formed of soft plastic or the like, having sufficient softness, diameter, and strength, to allow the capsule-type medical device 70 to be extracted from the stomach or small intestine through the mouth, or the large intestine from the anus, following inspection, without damaging the mucous membranes in the body cavity. The string 75 is formed in a soft fashion not to impede the rotational progress of the capsule main unit 70A. The string 75 is used by fixing the base end outside of the body. Also, the center of gravity of the capsule-type medical device 70 generally is upon the center axis 38 in the longitudinal direction of the capsule main unit 70A, as with in FIG. 3A and others.

The capsule-type medical device may be configured with the spiral portion 37 and the observation device 24 provided at the rear side of the capsule main unit in the direction of procession.

Figure 6A:
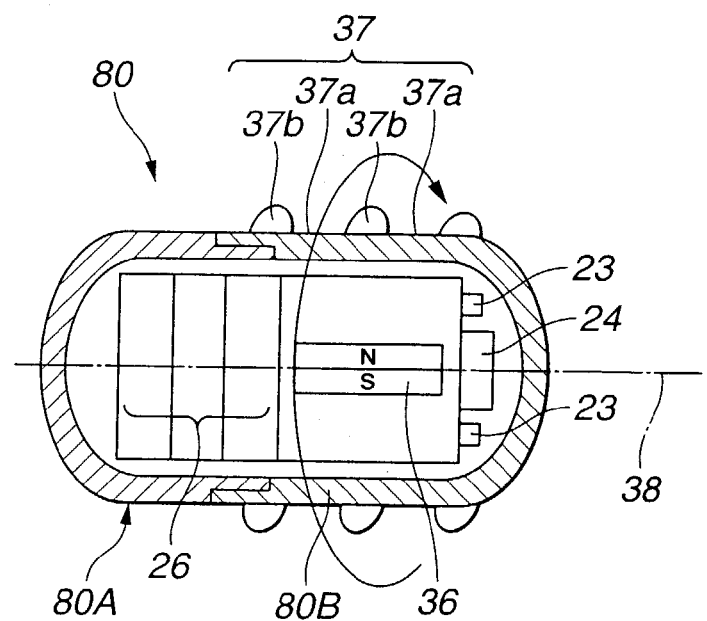
FIG. 6A is a cross-sectional diagram illustrating a capsule-type medical device wherein a spiral portion provided to the rear side with regard to the direction of progression is detachably provided, and an observation devices is provided on the rear side with regard to the direction of progression.
Figure 6B:
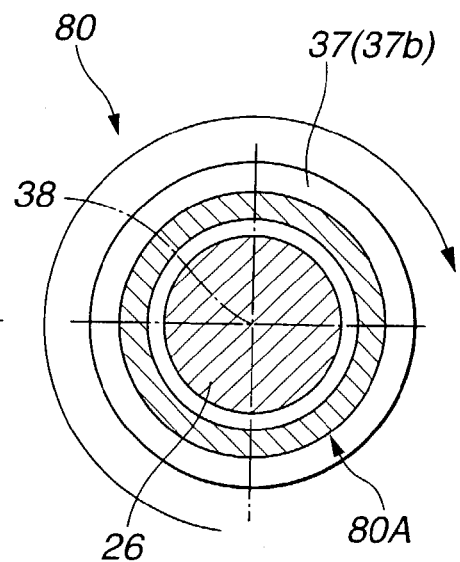
FIG. 6B is a transverse cross-sectional diagram of the arrangement shown in FIG. 6A.

That is to say, the capsule-type medical device 80 shown in FIGS. 6A and 6B comprises an exterior member 80B having a spiral portion 37 detachably formed on the rear side of the capsule main unit 80A in the direction of progression thereof (toward the left in FIG. 6A, in this case), as well as the observation device 24 along with the illumination device 23 in the backwards direction as to the direction of progression of the capsule main unit 80A.

Figure 7A:
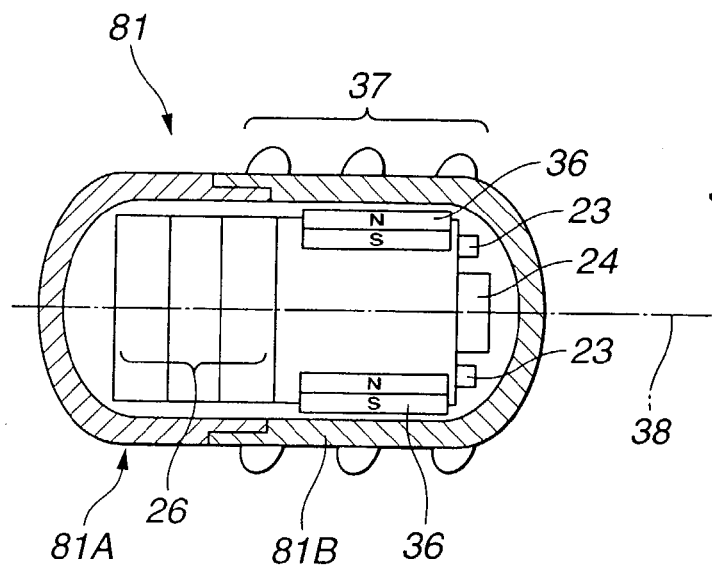
FIG. 7A is a cross-sectional view illustrating a capsule-type medical device wherein multiple magnets are symmetrically disposed on the center axis of the capsule main unit in the longitudinal direction.
Figure 7B:
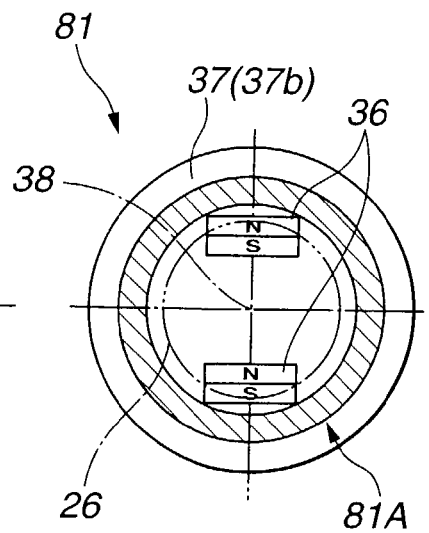
FIG. 7B is a transverse cross-sectional diagram of the arrangement shown in FIG. 7A.

Also, the capsule-type medical device 81 shown in FIGS. 7A and 7B comprises multiple magnets 36, and the magnets may be placed symmetrically across the longitudinal center axis 38 of the capsule main unit 81A. As with the capsule-type medical device 80, this capsule-type medical device 81 may be formed such that the exterior member 81B provided with the spiral portion 37 to the capsule main unit 81A is detachable.

Figure 8A:
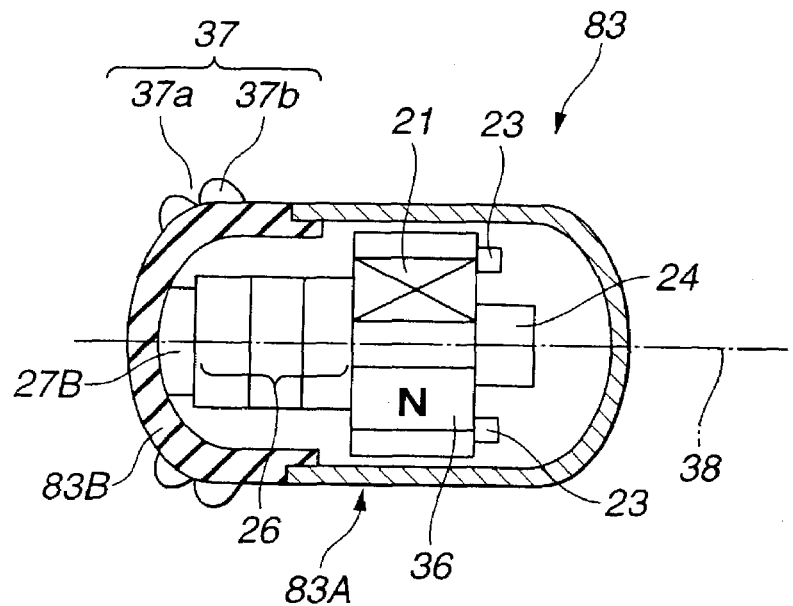
FIG. 8A is a cross-sectional view illustrating a capsule-type medical device wherein a spiral portion is detachably provided to the side at the direction of progression, while an observation device is provided on the rear side with regard to the direction of progression.
Figure 8B:
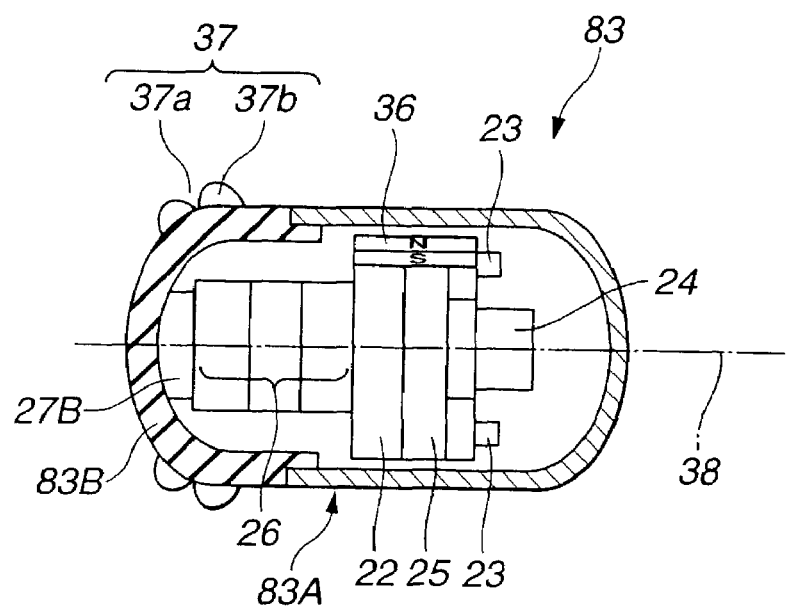
FIG. 8B is a cross-sectional diagram viewing the arrangement shown in FIG. 8A from the lower side of the drawing.

Also, as shown in FIGS. 8A and 8B, the capsule-type medical device may be formed such that the exterior member 83B provided with the spiral portion 37 to the capsule main unit 83A in the direction of progression thereof is detachable. Further, the observation device 24 may be provided along with the illumination device 23 in the backwards direction as to the direction of progression of the capsule main unit 83A.

Now, reference numeral 27B denotes a switch for tuning on and off electric power supplied from the batteries 26a in the battery unit 26.

The capsule-type medical device 83 shown in FIG. 8B has the magnet 36 provided parallel to the longitudinal center axis 38 of the capsule main unit 83A. The capsule-type medical device 83 comprises the digital signal processing circuit 25 and the wireless transmission/reception circuit 22 below the magnet 36.

Figure 9A:
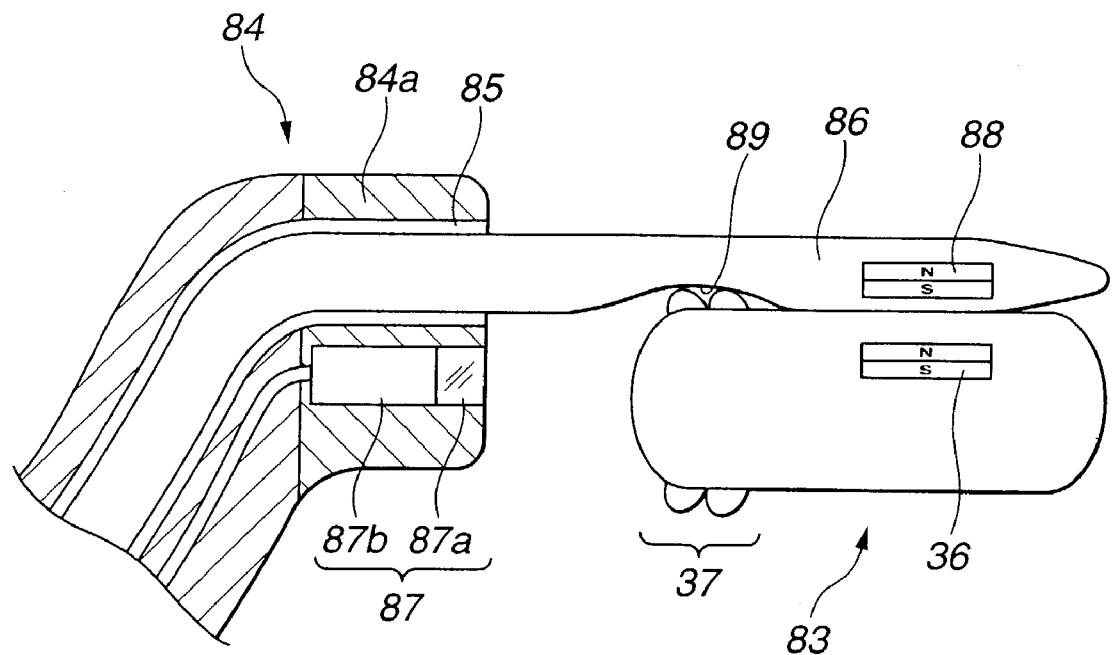
FIG. 9A is an explanatory diagram illustrating a capsule-type medical device which is recovered by a recovery tool inserted through a treatment device insertion channel of an endoscope.
Figure 9B:
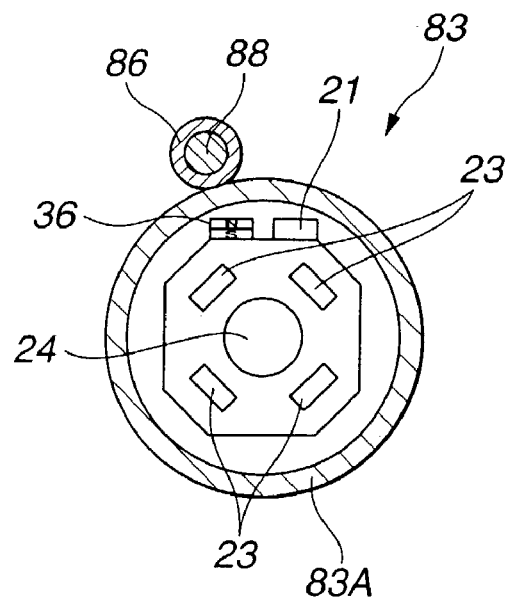
FIG. 9B is a transverse cross-sectional view at the tip side of the arrangement shown in FIG. 9A.

Also, the capsule-type medical device 83 is arranged so as to be recovered by a capsule recovery tool 86 inserted into a treatment tool insertion channel 85 of an endoscope 84, as shown in FIGS. 9A and 9B.

The endoscope 84 is arranged so that the capsule recovery tool 86 can be inserted through the treatment tool insertion channel 85. Reference numeral 87 denotes an observation device provided to a distal end 84a of the insertion portion of the endoscope 84. This observation device 87 is configured of an object optical system 87a and an imaging unit 87b comprising an imaging device provided at the imaging position of the object optical system 87a.

The capsule recovery tool 86 is formed as a flexible rod, with a magnet 88 for recovering the capsule-type medical device 83 provided at the tip thereof. The capsule recovery tool 86 also has a recessed portion 89 formed such that the spiral portion 37 of the capsule main unit 83A does not get in the way after the capsule-type medical device 83 is captured by the magnet 88.

Figure 10A:
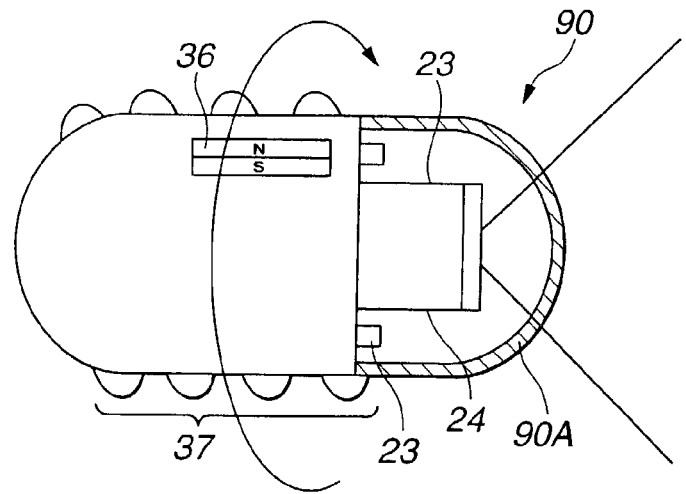
Figure 10B:
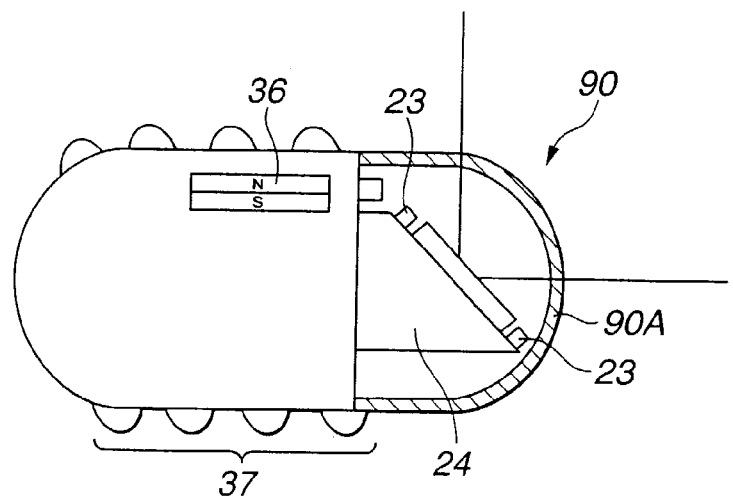
Figure 10C:
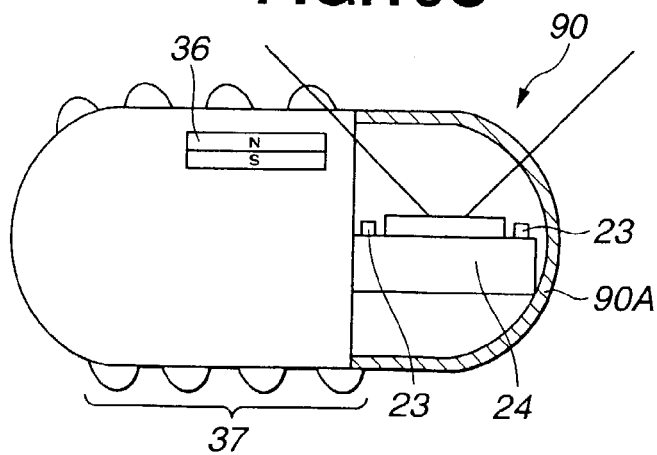

Also, an arrangement may be made wherein, as with the capsule-type medical device 90 shown in FIG. 10A, the capsule main unit 90A can be divided into the two portions of the portion where the observation device 24 is disposed, and the portion where the magnet 36 and the spiral portion 37 are provided. Thus, various combinations can be made for the capsule-type medical device 90 according to the use; an arrangement wherein the field of view of the observation device 24 is backwards as shown in FIG. 10A, an arrangement wherein the field of view of the observation device 24 is diagonally backwards as shown in FIG. 10B, and an arrangement wherein the field of view of the observation device 24 is sideways as shown in FIG. 10C.

Also, the capsule-type medical device may be arranged such that a portion having the spiral portion 37 is formed of a flexible member such as elastic rubber or the like, as shown in FIG. 11A, so as to form a flexible insertion portion to be inserted into the body cavity.

That is, with the capsule-type medical device 100 as shown in FIG. 11A, the portion provided with the spiral portion 37 may be formed as a flexible insertion portion (a flexible soft portion) 101 formed of a long and small-diameter flexible member, provided at one end of the rigid capsule main unit 10A, with two magnets 36a and 36b symmetrically disposed across the longitudinal center axis 38.

With this capsule-type medical device 100, the flexible insertion portion 101 has the same outer diameter as the outer diameter of one end of the generally-cylindrical capsule main unit 100A to which it is fastened by screwing, and the tip (end) side of the flexible insertion portion 101 is narrower than this outer diameter.

In this case, as shown in FIG. 11B, the capsule-type medical device 100 has the illumination device 23 thereof configured of multiple LEDs disposed in a ring-like shape around the observation device 24.

Also, an arrangement may be made with a ring-shaped magnet 36, as with the capsule-type medical device 100' having the flexible insertion portion 101 as shown in FIGS. 12A and 12B. With this capsule-type medical device 100', the base end of the flexible insertion portion 101 is connected to the rigid capsule main unit 100A by fitting or pressing.

Figure 13A:
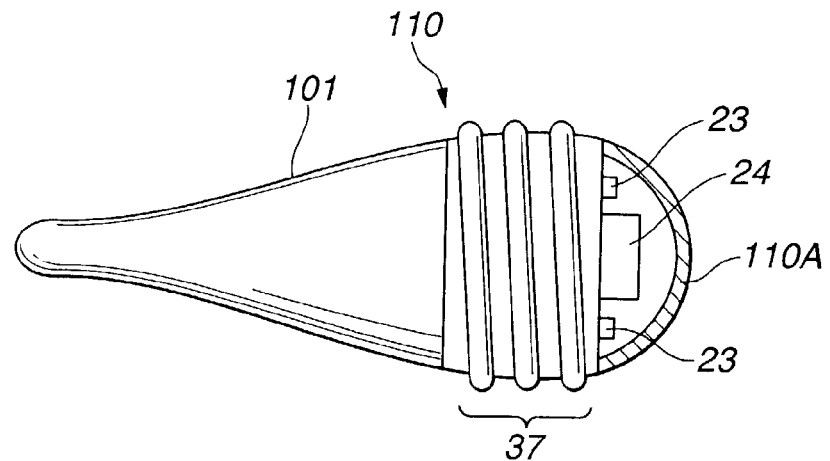
Figure 13B:
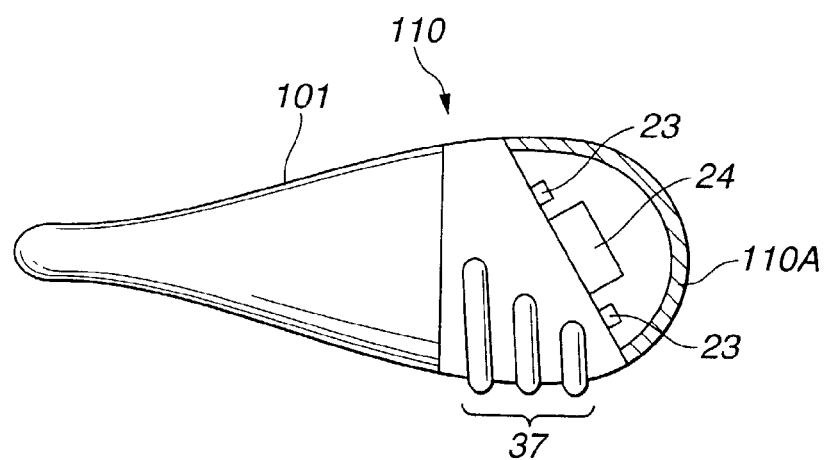
Figure 13C:
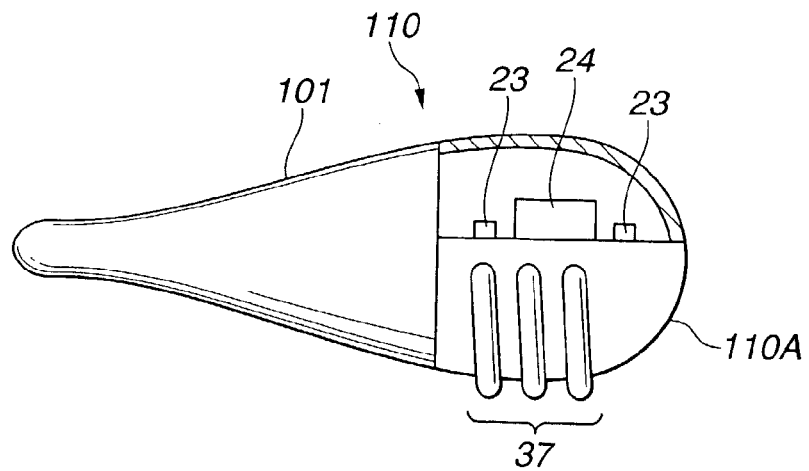

Also, instead of providing the spiral portion 37 on the flexible insertion portion 101, an arrangement may be made wherein the spiral portion 37 is provided on the rigid portion toward the rear on the side opposite to the flexible insertion portion 101 to which the flexible insertion portion 101 is connected (in the event that the flexible insertion portion 101 is at the front in the direction of advancing), as with the flexible insertion portion 101 as with the capsule-type medical device 110 shown in FIGS. 13A through 13C. In FIGS. 13A through 13C, the direction of advancing to the left, and the right side is the rear. The capsule-type medical device is swallowed, or inserted from the anus into the large intestine, so as to head in the direction of advancing.

In this case, various combinations can be made for the capsule-type medical device 110 according to the use; an arrangement wherein the field of view of the observation device 24 is backwards as shown in FIG. 13A, an arrangement wherein the field of view of the observation device 24 is diagonally backwards as shown in FIG. 13B, and an arrangement wherein the field of view of the observation device 24 is sideways as shown in FIG. 13C. That is to say, the flexible insertion portion 101 and the rigid capsule main unit 110A are separable.

With the capsule-type medical device 110 shown in FIG. 13A, the spiral portion 37 is provided over almost the entire perimeter of the rear side of the capsule main unit 110A. Also, with the capsule-type medical device 110 shown in FIG. 13B, the spiral portion 37 is provided over half of the rear side of the capsule main unit 110A in a diagonal manner, so as to allow observation in the diagonally backwards direction. Also, with the capsule-type medical device 110 shown in FIG. 13C, the spiral portion 37 is provided over half of the rear side of the capsule main unit 110A, so as to allow sideways observation.

Figure 14B:
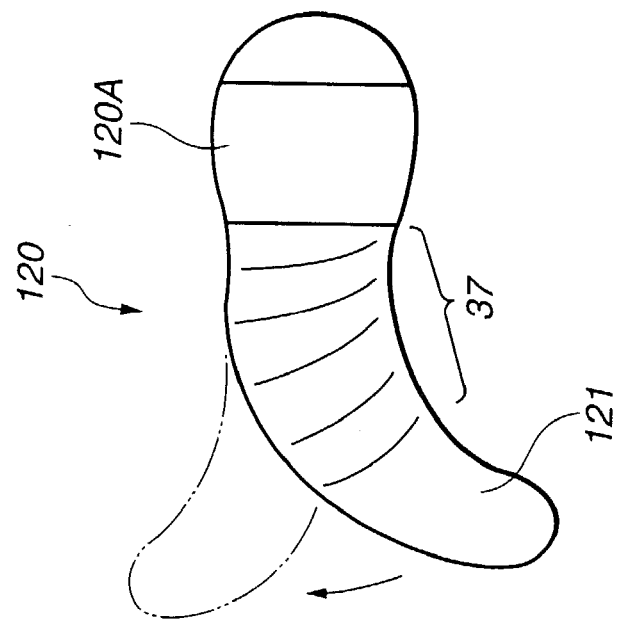
Figure 14A:
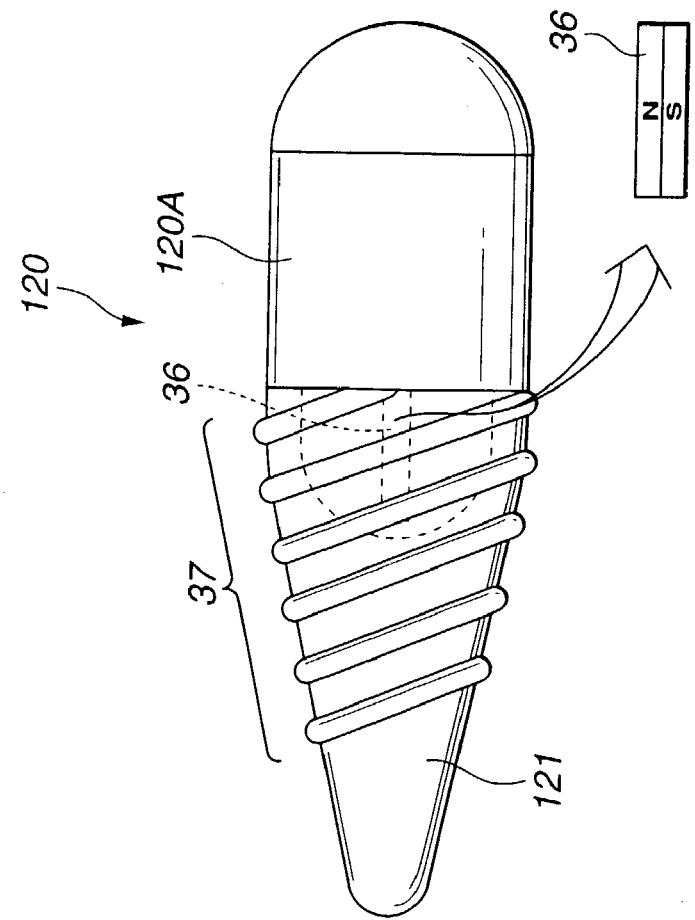
FIG. 14A is an explanatory diagram illustrating a capsule-type medical device wherein the flexible insertion portion is detachably mounted to the capsule main unit.

Also, the capsule-type medical device may have a configuration wherein the flexible insertion portion is detachably mountable to the capsule main unit as shown in FIG. 14A. That is to say, with the capsule-type medical device 120 shown in FIG. 14A, the flexible insertion portion 121 is detachably mountable to the capsule main unit 120A.

The flexible insertion portion 121 is soft, and thus easily bendable as shown in FIG. 14B. The flexible insertion portion 121 has a structure which is not readily stretched or compressed in the longitudinal direction, but readily bends in the direction generally orthogonal to the longitudinal direction.

Note that though the present embodiment has a wireless antenna 21 for performing transmission and reception with the control device 3, thus configuring a capsule-type medical device capable of examination, therapy, and/or treatment by passing through the body cavity under the control of the control device 3, the present invention is by no means restricted to this arrangement, and rather may be formed as a capsule-type medical device which is not provided with a wireless antenna 21 and wherein information (data) such as optical images are extracted following passing through the body cavity tract and being recovered outside of the body.

Second Embodiment

A second embodiment of the present invention will be described with reference to FIGS. 15 through 21. The present embodiment has been made to serve the same purpose as that of the first embodiment. The present embodiment also aims to pass through bent body cavity portions more smoothly.

The second embodiment comprises a flexible insertion portion (flexible soft portion), detachably mounted to a rigid capsule main unit. Other configurations are approximately the same as the first embodiment, so the same components will be denoted with the same reference numerals, and detailed description thereof will be omitted.

Figure 15:
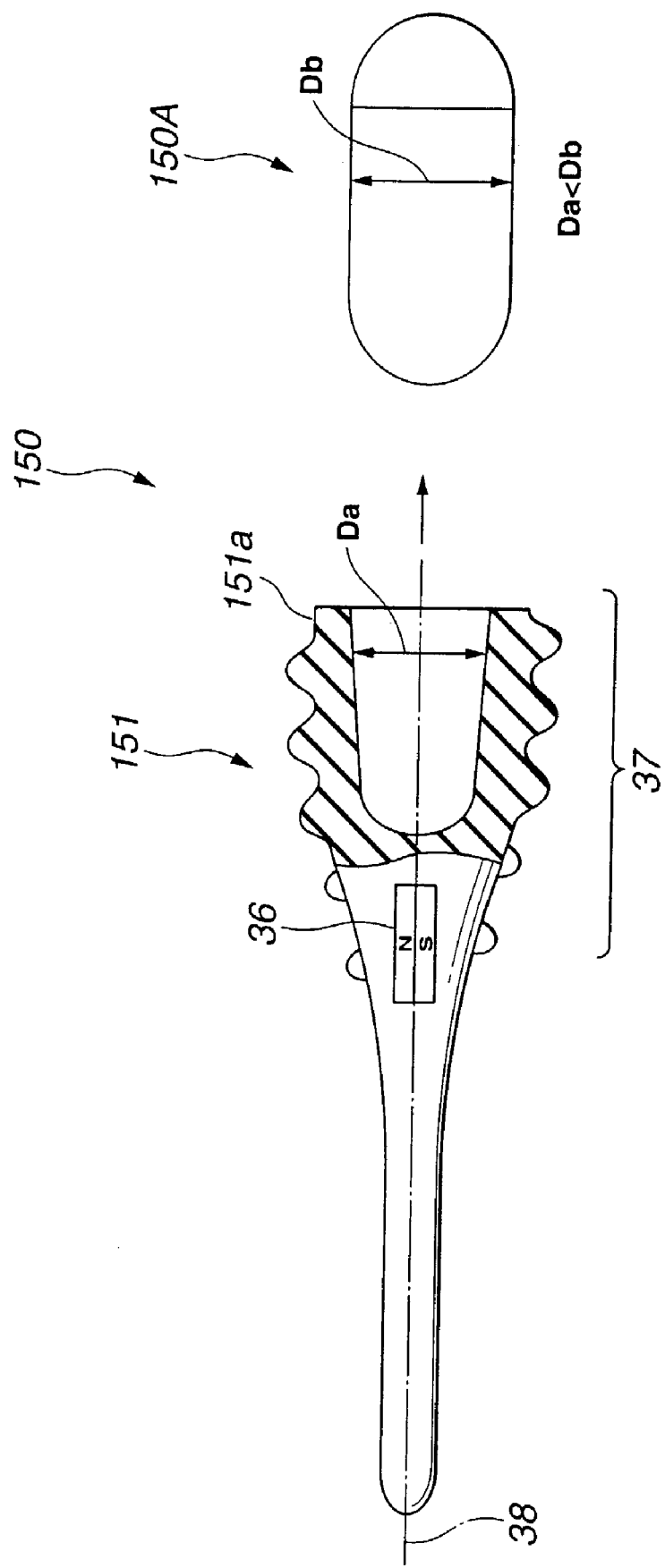

With the capsule-type medical device 150 according to the second embodiment as shown in FIG. 15, the bendable flexible insertion portion 151 is formed so as to be even longer and smaller in diameter than the flexible insertion portion 101 shown in FIG. 11A, for example, and is detachably mounted to the rigid capsule main unit 150A.

The flexible insertion portion 151 formed of elastic rubber or the like has the magnet 36 built in so as to be positioned on the longitudinal center axis 38, and has on the base side thereof a mounting portion 151a so as to be mounted onto the capsule main unit 150A. The flexible insertion portion 151 is mounted onto the capsule main unit 150A, thus configuring the capsule-type medical device 150.

In this case, the diameter Da of a recessed portion provided on the mounting portion 151a at the base side of the flexible insertion portion 151 is smaller than the diameter Db of the capsule main unit 150A, so that this recessed portion can be elastically attached to the capsule main unit 150A.

Figure 16:
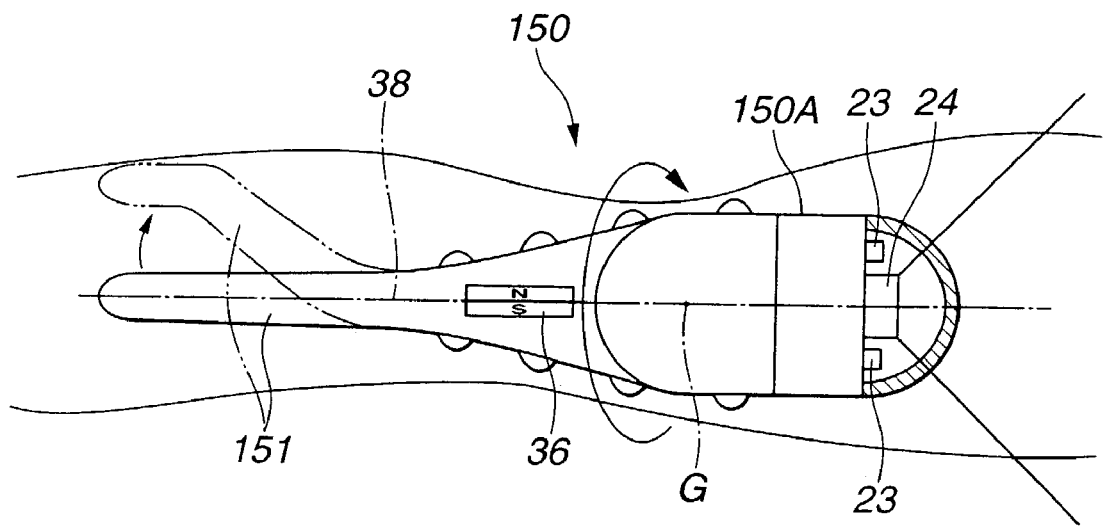

Also, the capsule-type medical device 150 is configured with the center of gravity G thereof generally matching the longitudinal center axis 38 of the capsule main unit 150A, as with the first embodiment (see FIG. 16).

Figure 18:
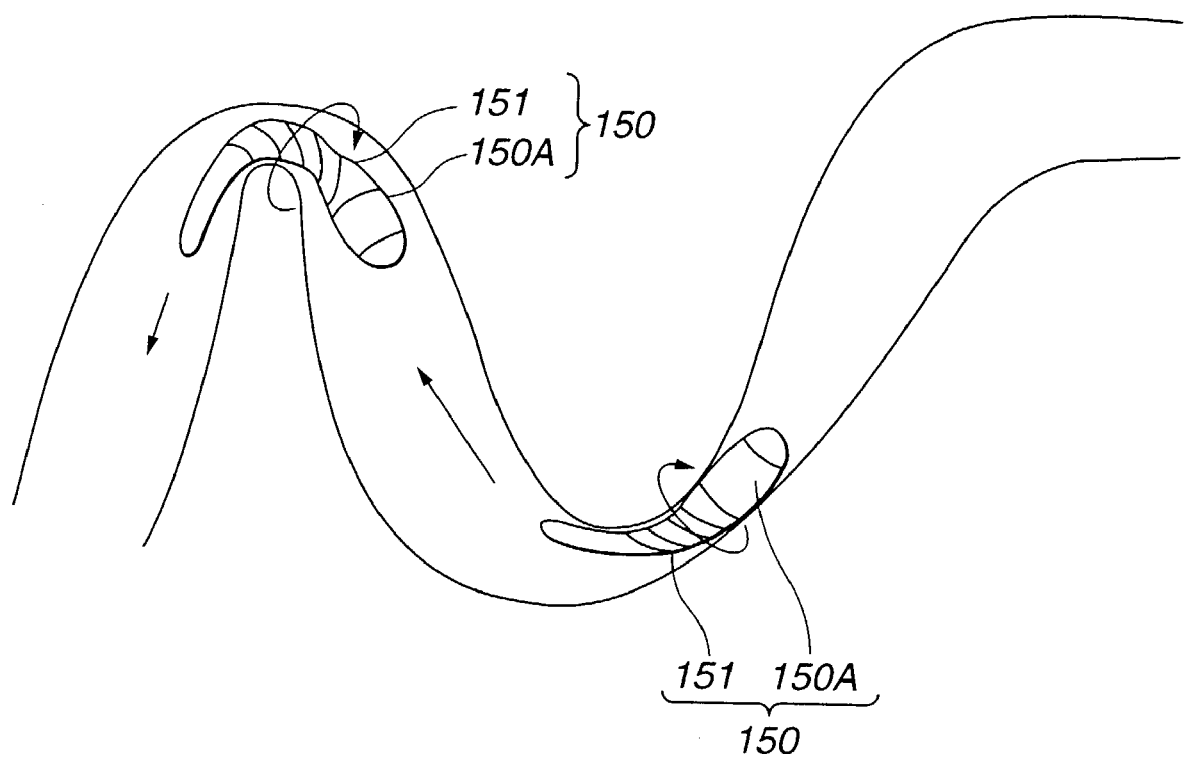

Also, as with the case of the flexible insertion portion 101, the flexible insertion portion 151 is configured so as to be bendable in the direction orthogonal to the longitudinal direction, with the side portion thereof being formed smaller in diameter than the outer diameter of the capsule main unit 150A, so as to have functions of bending following the bending body cavity tract such that the capsule main unit 150A at the rear end can smoothly proceed, as specifically indicated in FIG. 18.

Accordingly, the capsule-type medical device 150 moves through the body cavity with the flexible insertion portion 151 exploring the way to proceed, as shown in FIG. 16.

Figure 17:
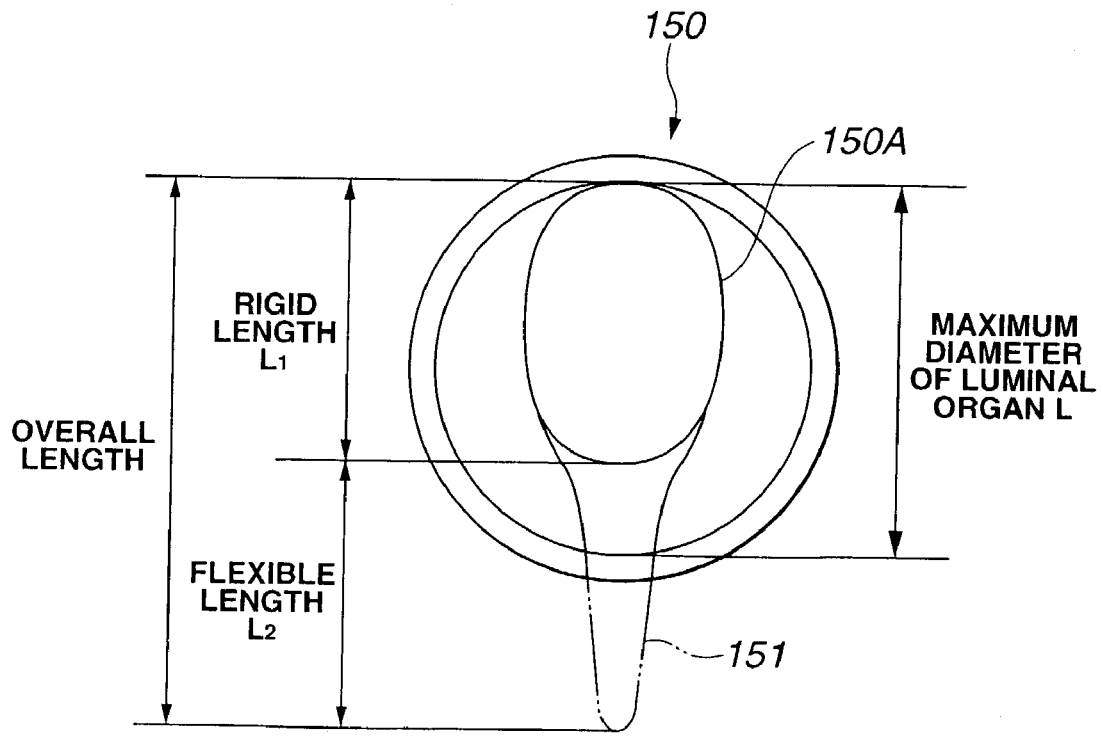

Now, the capsule-type medical device 150 may be configured so that, with regard to the maximum diameter L of a lumen organ such as the large intestine or the like, the relation between the rigid length L1 of the rigid capsule main unit 150A and the soft length L2 of the soft flexible insertion portion 151 is in the range of L1<L<L1+L2 as shown in FIG. 17.

In this case, the capsule-type medical device 150 is longer than the maximum diameter L of the lumen organ and moreover the length of the rigid portion is short, so the direction thereof does not change in the lumen, and further, rotations from the magnet 36 are converted directly into propulsion, so the rotational force can be efficiently converted into propulsion, and smoothly move through the lumen.

Also, the capsule-type medical device 150 rotates due to the magnet 36 at bent and narrow portions in the lumen such as the small intestine and large intestine as shown in FIG. 18, with the flexible insertion portion 151 finding its way ahead, and the capsule main unit 150A following the flexible insertion portion 151 can readily pass through, as well.

Accordingly, with the present embodiment, eccentric movement can be suppressed, and the capsule-type medical device 150 can be smoothly propelled to the target portion, as with the first embodiment. In this case, the flexible insertion portion 151 is formed even longer and smaller in diameter, so eccentric movement can be suppressed even further.

With the present embodiment, the flexible insertion portion 151 at the tip bends following the shape of bent tract in the lumen, and thus acts to allow the trailing capsule main unit 150A to change direction so as to smoothly pass. The capsule-type medical device 150 thus smoothly passes through bent lumen portions as well, thereby reducing the time for medical examination and/or treatment.

Figure 19:
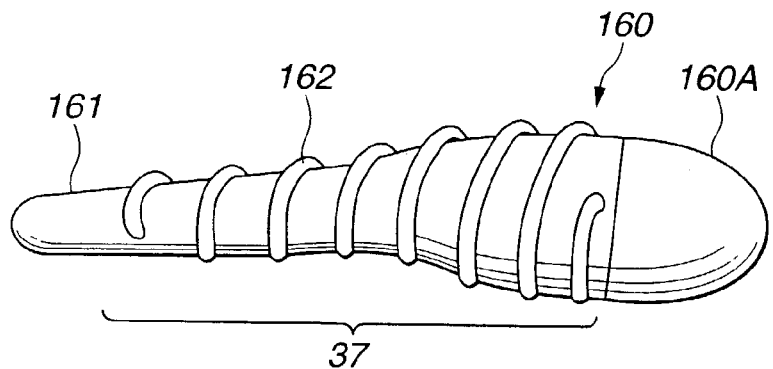

Also, an arrangement may be made wherein a wire-like member 162 is fixed by adhesions to the outer perimeter of the flexible insertion portion 161 to form the spiral portion 37, as with the capsule-type medical device 160 shown in FIG. 19. With such an arrangement for the capsule-type medical device 160, the spiral portion 37 can be readily provided to the flexible insertion portion 161. The wire-like member 162 may be formed of an elastic member such as rubber, shaped into a wire-like form.

Figure 20:
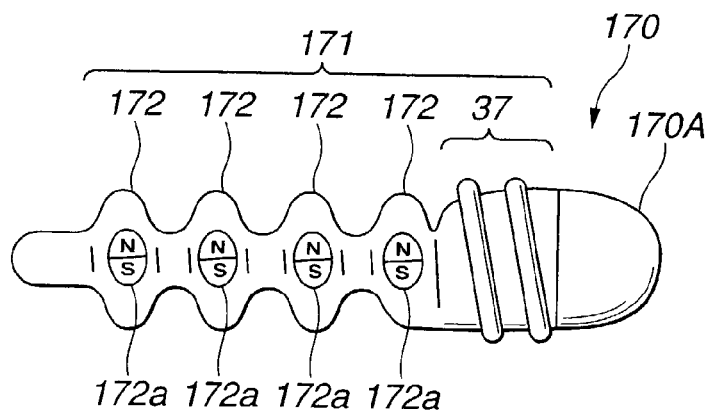
Figure 21:
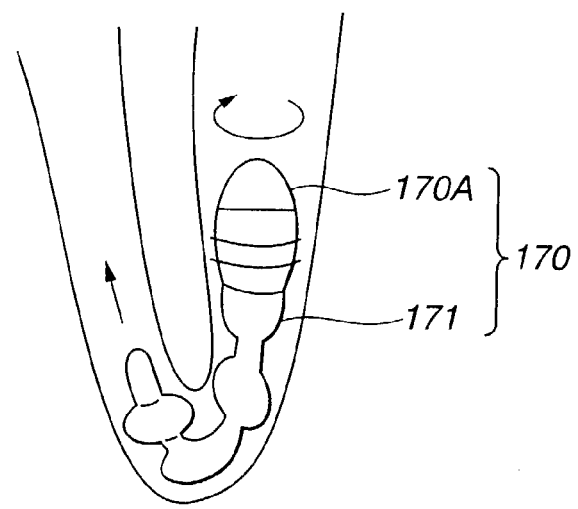

Also, an arrangement may be made for the capsule-type medical device 170 wherein multiple ball-shaped magnets 172a are built into the flexible insertion portion 171 so as to form multiple ball-shaped protrusions 172, as shown in FIG. 20. The flexible insertion portion 171 is soft, so the capsule-type medical device 170 can go to the depths of bent portions in the tubular organs such as the small intestine or large intestine, while rotating, as indicated in FIG. 21.

Third Embodiment

A third embodiment of the present invention will be described with reference to FIGS. 22 and 23. The primary objects of the present embodiment are approximately the same as those of the first and second embodiments. Also, the present embodiment also aims to enable medical examination and/or treatment to be performed even more efficiently.

With the third embodiment, two capsule main units are provided, a leading-side rigid portion and a trailing-side rigid portion, with the two rigid portions being connected with a string-like material covered with a soft elastic materials such as urethane or silicon rubber or the like which smoothly changes external form as shown in the drawings, for example. Other configurations are approximately the same as the first embodiment, so the same components will be denoted with the same reference numerals, and detailed description thereof will be omitted.

Figure 22:
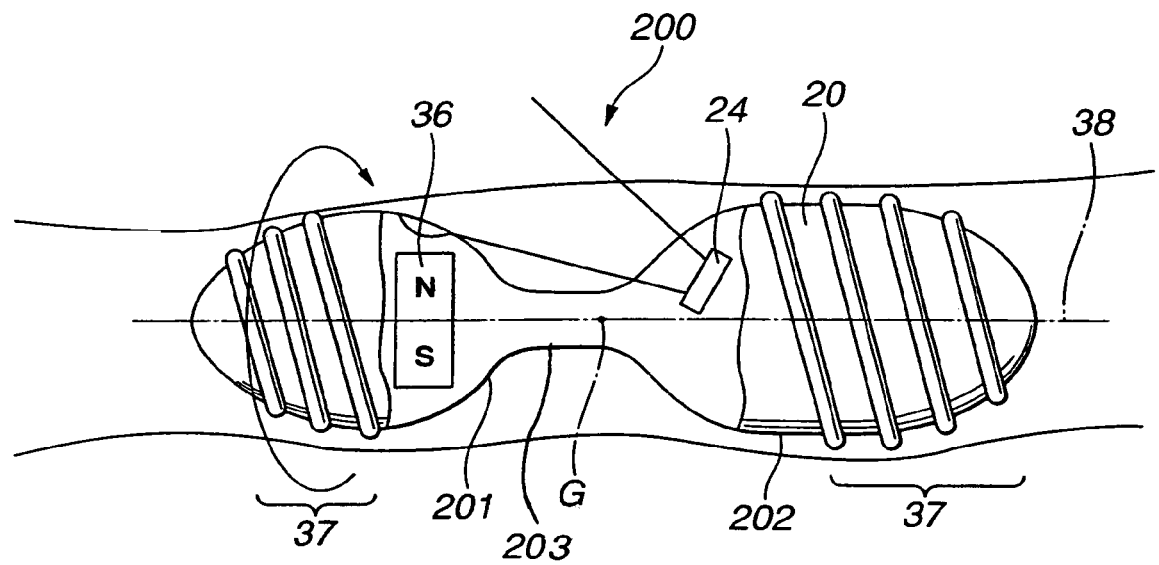
Figure 23:
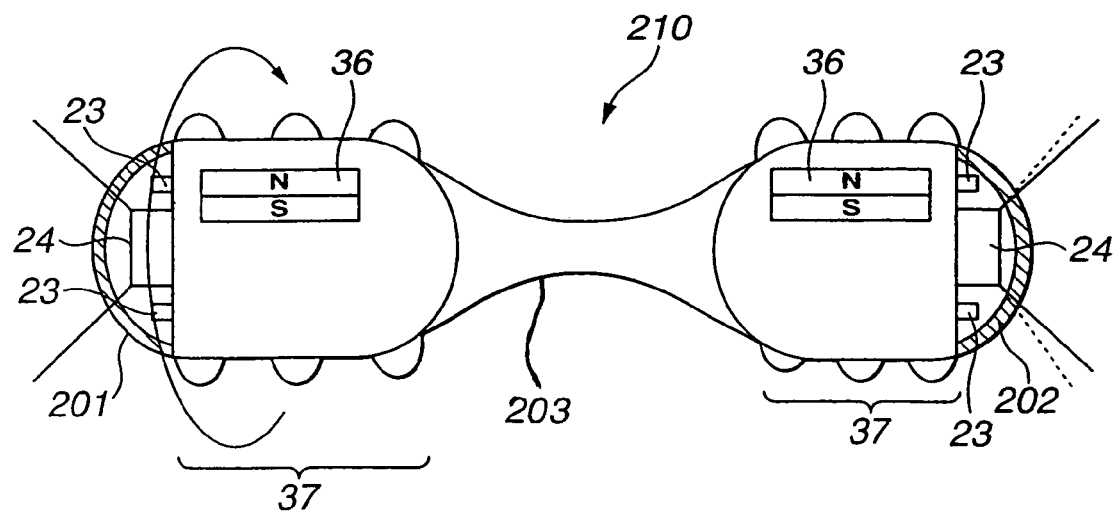

With the capsule-type medical device 200 according to the third embodiment, two capsule main units 200A are provided, a leading-side rigid portion 201 and a trailing-side rigid portion 202, with the two rigid portions 201 and 202 being connected with a string-like member 203 as shown in FIG. 22. Also, the capsule-type medical device 200 is configured with the center of gravity G thereof generally matching the longitudinal center axis 38 of the capsule main unit 200A, as with the first embodiment.

Also, the capsule-type medical device 200 comprises the spiral portions 37 on both the leading-side rigid portion 201 and the trailing-side rigid portion 202. Further, the observation device 24 is configured so as to have a field of view looking diagonally forwards at the tip of the trailing-side rigid portion 202.

According to such a configuration, the capsule-type medical device 200 can obtain a good observation field of view even if in close contact with the lumen.

That is to say, the capsule-type medical device 200 proceeds while rotating, so the inner walls can be efficiently observed, and medical examination and/or treatment can be performed efficiently.

Also, with the capsule-type medical device 200, a portion of the protrusions formed on the leading-side rigid portion 201 also come into the field of view of the observation device 24, so a mark is made in this field of view to indicate the position (polarity) of the magnet 36.

Also, an arrangement may be made for the capsule-type medical device 210 wherein magnets 36, observation devices 24, and illumination devices 23, are provided to both the leading-side rigid portion 201 and trailing-side rigid portion 202 provided with the spiral portions 37. In this case, propulsion can be generated for the capsule-type medical device 210 as long as one of the spiral portions 37 comes into contact with the inner walls of the lumen or with luminal fluids, regardless of whether the other spiral portion 37 is in contact with something.

This means that the capsule-type medical device 210 can be propelled efficiently, and medical examination and/or treatment can be performed efficiently. Also, providing observation means on both sides allows medical examination and/or treatment (image-taking, in this case) to be performed even in the event that the image from one is insufficient, by compensating with the image from the other. In order to expand this function, an arrangement may be made wherein the observation and illumination range of the observation devices 24 and illumination devices 23 of the trailing-side rigid portion 202 is changed as to the observation and illumination range of the observation devices 24 and illumination devices 23 of the leading-side rigid portion 201, for example, widening the range as indicated by the dotted lines (only the range of observation is indicated, for sake of simplicity).

In this case, two types of imaged pictures with different observation ranges are obtained, so medical examination and/or treatment can be performed more efficiently.

According to the present invention described above, a capsule-type medical device which can smoothly reach a target position through the lumen tract without useless motions such as eccentric movement can be realized. Further, according to the present invention, magnetic guiding efficiency is improved by reducing the unnecessary movement, so a capsule-type medical device wherein one or both of the magnet within the capsule main unit and the external magnet can be reduced in size.

Having described the preferred embodiments of the invention referring to the accompanying drawings, it should be understood that the present invention is not limited to those precise embodiments, and various changes, combinations, and modifications thereof could be made by one skilled in the art without departing form the spirit or scope of the invention as defined in the appended claims.

What is claimed is:

1. A capsule-type medical device comprising:
    a capsule main unit for performing medical acts such as examination, therapy, and/or treatment within a subject;
    a magnet provided to at least a part of the capsule main unit, for being magnetically acted upon by external magnetism outside of the subject;
    a flexible insertion portion, at least a portion thereof being covered with flexible rubber, the flexible insertion portion being formed on at least one end of the capsule main unit and formed narrower in diameter at the end thereof than an outer diameter of the capsule main unit;
    a propulsion generating unit provided on at least one of: (a) at least a part of an outer perimeter of the capsule main unit and (b) the flexible insertion portion, for converting rotating motion due to the magnet into a propulsion force; and
    a function means for performing one or more medical acts, wherein
    the function means is provided on one end of the capsule main unit and the flexible insertion portion is provided on another end;
    the magnet is arranged on a center axis of the capsule main unit and magnetized with respect to a plane including the center axis as a boundary, so as to have an N-pole on one side and an S-pole on another side.

2. A capsule-type medical device according to claim 1, wherein
    the propulsion generating unit is further comprised of a spiral portion.

3. A capsule-type medical device according to claim 2, wherein
    the propulsion generating unit consists of a base and the spiral portion formed on the base, and
    the base is detachably mounted to the capsule main unit.

4. A capsule-type medical device according to claim 2, wherein the spiral portion has spiral-like protrusions formed by a wire-like member protruding on an outer face of the capsule main unit.

5. A capsule-type medical device according to claim 2, wherein the spiral portion is made up of spiral grooves and spiral ridges.

6. A capsule-type medical device according to claim 1, wherein, a plurality of observation means are provided near each end of the capsule main unit in a longitudinal direction.

7. A capsule-type medical device according to claim 6, wherein one of the plurality of observation means has an observation field of view facing approximately sideways from the capsule main unit.

8. A capsule-type medical device according to claim 1, wherein the capsule main unit is configured of a plurality of rigid portions and a narrow-diameter soft portion connecting the plurality of rigid portions, with the propulsion generating unit provided to at least one of the plurality of rigid portions.

9. A capsule-type medical device according to claim 1, wherein the center of gravity of the capsule main unit is generally placed upon a longitudinal center axis of the capsule main unit.

10. A capsule-type medical device according to claim 1, the capsule main unit comprising:
    a rigid portion; and
    a soft portion connected to the rigid portion and having a form wherein an external diameter thereof gradually becomes smaller the farther away from the rigid portion;
    wherein a total length of the capsule main unit is longer than a maximum luminal diameter of the large intestine of the subject.

11. A capsule-type medical device according to claim 1, further comprising a recovery tool formed as a flexible rod, the recovery tool having at least one of a magnet and magnetic substance provided proximate a distal end thereof for generating magnetic pull as to a peripheral polarity of the at least one of the magnet and magnetic substance to draw the capsule main unit by magnetic pull.

12. The capsule-type medical device according to claim 1, wherein the external magnetism outside of the subject is a rotary magnetism.

13. A capsule-type medical device according to claim 1, wherein the magnet is arranged so that the N-pole and the S-pole may provide a single orientation.

14. A capsule-type medical device according to claim 1, wherein the propulsion generating unit consists of a base and the spiral portion formed on the base, and the base is detachably mounted to the capsule main unit.

15. A capsule-type medical device according to claim 2, wherein the center of gravity of the capsule main unit is generally placed upon a longitudinal center axis of the capsule main unit.

16. A capsule-type medical device according to claim 2, wherein the external magnetism outside of the subject is a rotary magnetism.

17. A capsule-type medical device comprising:
a capsule main unit for performing medical acts such as examination, therapy, and/or treatment within a subject;
a magnet provided to at least a part of the capsule main unit, for being magnetically acted upon by external magnetism outside of the subject;
a flexible insertion portion, at least a portion thereof being covered with flexible rubber, the flexible insertion portion being formed on at least one end of the capsule main unit and formed narrower in diameter at the end thereof than an outer diameter of the capsule main unit;
a propulsion generating unit provided on at least one of: (a) at least a part of an outer perimeter of the capsule main unit and (b) on the flexible insertion portion, for converting rotating motion due to the magnet into a propulsion force; and
a function means for performing one or more medical acts, wherein
the function means is provided on one end of the capsule main unit and the flexible insertion portion is provided on another end and
the function means is an observation device.

18. A capsule-type medical device according to claim 17, wherein the observation device has an observation field of view facing approximately sideways relative to a longitudinal axis of the capsule main unit.

19. A capsule-type medical device comprising:
a capsule main unit having functions for performing medical acts such as examination, therapy, and/or treatment within a subject;
one or more magnets provided to the capsule main unit, for being magnetically acted upon by external magnetism outside of the subject;
a propulsion generating unit for converting rotating motion due to the one or more magnets into propulsion force; and
a recovery tool formed as a flexible rod, the recovery tool having at least one of a magnet and magnetic substance provided proximate a distal end thereof for generating magnetic pull as to a peripheral polarity of the at least one of the magnet and magnetic substance to draw the capsule main unit by magnetic pull;
wherein
the center of gravity of the capsule main unit is generally placed upon a longitudinal center axis of the capsule main unit,
the propulsion generating unit has spiral protrusions protruding on an outer face of the capsule main unit and
the recovery tool has a recessed portion formed to provide clearance for the spiral protrusions when the capsule main unit is captured by the recovery tool.

20. A capsule-type medical device according to claim 19, wherein the one or more magnets comprise a plurality of magnets that are disposed on the longitudinal center axis with spacing therebetween.

\* \* \* \* \*

UNITED STATES PATENT AND TRADEMARK OFFICE
CERTIFICATE OF CORRECTION

PATENT NO. : 7,578,788 B2
APPLICATION NO. : 10/395745
DATED : August 25, 2009
INVENTOR(S) : Yokoi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 381 days.

Signed and Sealed this

Seventh Day of September, 2010

David J. Kappos
*Director of the United States Patent and Trademark Office*